United States Patent
Anderson et al.

(10) Patent No.: US 6,280,966 B1
(45) Date of Patent: *Aug. 28, 2001

(54) INDICATORS OF ALTERED MITOCHONDRIAL FUNCTION IN PREDICTIVE METHODS FOR DETERMINING RISK OF TYPE 2 DIABETES MELLITUS

(75) Inventors: Christen M. Anderson, Encinitas; Robert E. Davis, San Diego, both of CA (US)

(73) Assignee: Mitokor, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/521,407

(22) Filed: Mar. 8, 2000

Related U.S. Application Data

(63) Continuation of application No. 09/303,816, filed on Apr. 30, 1999.

(51) Int. Cl.[7] ............... C12Q 1/32; C12Q 1/54; C12Q 1/00; C12Q 1/50
(52) U.S. Cl. ............... 435/26; 435/14; 435/4; 435/7
(58) Field of Search .................. 435/26, 14, 4, 435/17

(56) References Cited

U.S. PATENT DOCUMENTS

| 5,840,493 | 11/1998 | Davis et al. ............... 435/6 |
| 5,888,498 | 5/1999 | Davis et al. ............... 424/93.21 |

FOREIGN PATENT DOCUMENTS

WO 98/17826  4/1998  (WO) .

OTHER PUBLICATIONS

Anderson, "Mitochondrial Dysfunction in Diabetes Mellitus," *Drug Development Research* 46:67–79, 1999.

Anderson et al., "Sequence and Organization of the Human Mitochondrial Genome," *Nature* 290:457–465, 1981.

Antonetti et al., "Increased Expression of Mitochondrial–Encoded Genes in Skeletal Muscle of Humans with Diabetes Mellitus," *J. Clin. Invest.* 95:1383–1388, 1995.

Baynes, "Role of Oxidative Stress in Development of Complications in Diabetes," *Diabetes* 40:405–412, 1991.

Baynes and Thorpe, "Role of Oxidative Stress in Diabetic Complications. A New Perspective on an Old Paradigm," *Diabetes* 48:1–9, 1999.

Belch et al., "Oxidative Stress is Present in Atherosclerotic Peripheral Arterial Disease and Further Increased by Diabetes Mellitus," *International Angiology* 14(4):385–388, 1995.

(List continued on next page.)

Primary Examiner—Louise N. Leary
(74) Attorney, Agent, or Firm—SEED Intellectual Property Law Group, PLLC

(57) ABSTRACT

The present invention relates to improved diagnostic methods for early detection of a risk for developing type 2 diabetes mellitus in humans, and screening assays for therapeutic agents useful in the treatment of type 2 diabetes mellitus, by comparing the levels of one or more indicators of altered mitochondrial function. Indicators of altered mitochondrial function include enzymes such as mitochondrial enzymes and ATP biosynthesis factors. Other indicators of altered mitochondrial function include mitochondrial mass, mitochondrial number and mitochondrial DNA content, celullar responses to elevated intracellular calcium and to apoptogens, and free radical production. Methods of treating, and of stratifying, human patients as such methods relate to disclosed indicators of altered mitchondrial function are also provided.

16 Claims, 4 Drawing Sheets

OTHER PUBLICATIONS

Clapham, "Calcium Signaling," *Cell 80:*259–268, 1995.

Cruz–Orive and Weibel, "Recent Stereological Methods for Cell Biology: A Brief Survey," *Am. J. Physiol. 258:*L148–L156, 1990.

Davis et al., "Mutations in Mitochondrial Cytochrome c Oxidase Genes Segregrate with Late–Onset Alzheimer Disease," *Proc. Natl. Acad. Sci. USA 94:*4526–4531, 1997.

Fahy et al., "Multiplex Fluorescene–Based Primer Extension Method for Quantitive Mutation Analysis of Mitochondrial DNA and its Diagnostic Application for Alzheimer's Disease," *Nucleic Acids Research 25*(15):3102–3109, 1997.

Ghosh et al., "Longitudinal Study of a Heteroplasmic 3460 Leber Hereditary Optic Neuropathy Family by Multiplexed Primer–Extension Analysis and Nucleotide Sequencing," *Am. J. Hum. Genet. 58:*325–334, 1996.

Gómez–Diaz et al., "Ascorbate Stabilization Is Stimulated in $\rho°$HL–60 Cells by $CoQ_{10}$ Increase at the Plasma Membrane," *Biochemical And Biophysical Research Communications 234:*79–81, 1997.

Gross et al., "The Effect of Streptozotocin–Induced Diabetes on Oxidative Phosphorylation and Related Reactions in Skeletal Muscle Mitochondria," *Horm. Metab. Res. 4*(1–7):1–7, 1972.

Hinokio et al., "Oxidative Damage to Mitochondrial DNA: Its Relationship to Diabetic Complication," *Diabetes 46*(Supplement 1):173A, Abstract No. 0665, 1997.

Huang et al., "Identification of Differentially Expressed Genes in NIDDM by cDNA Differentially Display," *Diabetologia 39*(Supplemental 1):A72, Abstract No. 265, 1996.

Huang et al., "Is Abnormal Expression of Mitochondrial Genes in Skeletal Muscle Genetically Determined?," *Diabetologia 40*(Supplemental 1):A 168, Abstract No. 657, 1997.

Kahn, "Insulin Action, Diabetogenes, and the Cause of Type II Diabetes," *Diabetes 43:*1066–1084, 1994.

Kennedy and Lyons, "Glycation, Oxidation, and Lipoxidation in the Development of Diabetic Complications," *Metabolism 46*(12):14–21, 1997.

Kruszynska et al., "Regulation of Skeletal Muscle Hexokinase II by Insulin in Nondiabetic and NIDDM Subjects," *Diabetes 47:*1107–1113, 1998.

Lee, "Yonchon Experiences: Epidemiological Search for the Diabetogenic Factors," in *Proceedings of the Course (The First Asia–Pacific Diabetes Epidemiology Training Course)* at Young–In, Korea, Jul. 10–19, 1998, pp. 111–114.

Lee et al., "Decreased Mitochondrial DNA Content in Peripheral Blood Precedes the Development of Non–Insulin–Dependent Diabetes Mellitus," *Diabetes Research and Clinical Practice 42:*161–167, 1998.

Lee et al., "Peripheral Blood Mitochondrial DNA Contents Can Predict the Development of Diabetes," *Diabetes 46*(Supplement 1):175A, Abstract No. 0673, 1997.

Liang et al., "Increased Prevalence of Mitochondrial DNA Deletions in Skeletal Muscle of Older Individuals With Impaired Glucose Tolerance," *Diabetes 46:*920–923, 1997.

Lightowlers et al., "Mammalian Mitochondrial Genetics: Heredity, Heteroplasmy And Disease," *TIG 13*(11):450–455, 1997.

Liu and Roth, "Binding of SH2 Containing Proteins to the Insulin Receptor: A New Way for Modulating Insulin Signalling," *Molecular Cellular Biochemistry 182:*73–78, 1998.

Lopez et al., "Numt, a Recent Transfer and Tandem Amplification of Mitochondrial DNA to the Nuclear Genome of the Domestic Cat," *Journal Of Molecular Evolution 39:*174–190, 1994.

Marchetti et al., "Apoptosis–Associated Derangement of Mitochondrial Function in Cells Lacking Mitochondrial DNA," *Cancer Research 56:*2033–2038, 1996.

Midaoui et al., "Effect of Physical Training on Mitochondrial Function in Skeletal Muscle of Normal and Diabetic Rats," *Metabolism 45*(7):810–816, 1996.

Miller et al., "Creation and Characterization of Mitochondrial DNA–Depleted Cell Lines with "Neuronal–Like" Properties," *Journal of Neurochemistry 67:*1897–1907, 1996.

Moley et al., "Hyperglycemia Induces Apoptosis in Pre–Implantation Embryos Through Cell Death Effector Pathways," *Nature Medicine 4*(12):1421–1424, 1998.

Moraes et al., "mtDNA Depletion With Variable Tissue Expression: A Novel Genetic Abnormality In Mitochondrial Diseases," *Am. J. Hum. Genet. 48:*492–501, 1991.

Nakamura et al., "A Novel Homoplasmic Point Mutation at Mitochondrial DNA (mtDNA) Nucleotide 3308 in a Family with Atypical Diabetes Mellitus (ADM) of African Americans (AA)," *Diabetes 46*(Supplement 1):175A, Abstract No. 0673, 1997.

Parfait et al., "Coamplification Of Nuclear Pseudogenes And Assessment Of Heteroplasmy Of Mitochondrial DNA Mutations," *Biochemical And Biophysical Research Communications 247:* 57–59, 1998.

Parker, Jr. and Parks, "Abnormalities of the Electron Transport Chain in Idiopathic Parkinson's Disease," *Ann. Neurol. 26:*719–723, 1989.

Schwerzmann et al., "Molecular Architecture of the Inner Membrane of Mitochrondria from Rat Liver: A Combined Biochemical and Stereological Study," *The Journal Of Cell Biology 102:*97–103, 1986.

Sepehrina et al., *Amer. J. Med. Genetics 56*(2):198–202, 1995.

Serradas et al., "Mitochondrial Deoxyribonucleic Acid Content Is Specifically Decreased in Adult, But Not Fetal, Pancreatic Islets of the Goto–Kakizaki Rat, a Genetic Model of Noninsulin–Dependent Diabetes," *Endocrinology 136*(12):5623–5631, 1995.

Simoneau and Kelley, "Altered Glycolytic and Oxidative Capacities of Skeletal Muscle Contribute to Insulin Resistance in NIDDM," *J. Appl. Physiol. 83*(1):166–171, 1997.

Soejima et al., "Mitochondrial DNA Is Required for Regulation of Glucose–stimulated Insulin Secretion in a Mouse Pancreatic Beta Cell Line, MIN6," *The Journal of Biological Chemistry 271*(42):26194–26199, 1996.

Spiegelman, "PPAR–$\gamma$: Adipogenic Regulator and Thiazolidinedione Receptor," *Diabetes 47:*507–514, 1998.

Tatuch et al., "The 8993 mtDNA Mutation: Heteroplasmy And Clinical Presentation In Three Families," *Eur. J. Hum. Genet. 2*(1):35–43, 1994.

The Expert Committee On The Diagnosis And Classification Of Diabetes Mellitus, "Report of the Exert Committee on the Diagnosis and Classification of Diabetes Mellitus," *Diabetes Care 22*(Supplement 1):S5–S19, 1999.

Traverso et al., "Immunological Evidence for Increased Oxidative Stress in Diabetic Rats," *Diabetologia 41:*265–270, 1998.

Van den Bogert et al., "Regulation Of The Expression Of Mitochondrial Proteins: Relationship Between mtDNA Copy Number And Cytochrome–c Oxidase Activity In Human Cells And Tissues," *Biochimica et Biophysica Acta 1144:*177–183, 1993.

Velázquez et al., "Relation of Lipid Peroxides to Macrovascular Disease in Type 2 Diabetes," *Diabetic Medicine 8:*752–758, 1991.

Vestergaard et al., "Impaired Activity and Gene Expression of Hexokinase II in Muscle from Non–Insulin–Dependent Diabetes Mellitus Patients," *J. Clin. Invest. 96:*2639–2645, 1995.

Vicent et al., "Alterations in Skeletal Muscle Gene Expression of ob/ob Mice by mRNA Differential Display," *Diabetes 47:*1451–1458, 1998.

Vondra et al., "Enyme Activities in Quadriceps Femoris Muscle of Obese Diabetic Male Patients," *Diabetologia 13:*527–529, 1977.

Walker et al., "[2] Structural Analysis of NADH: Ubiquinone Oxidoreductase from Bovine Heart Mitochondria," *Methods in Enzymology 260:*14–34, 1995.

Wallace et al., "Ancient mtDNA Sequences in the Human Nuclear Genome: A Potential Source of Errors in Identifying Pathogenic Mutations," *Proc. Natl. Acad. Sci. USA 94:*14900–14905, 1997.

Williams et al., "Regulation Of Nuclear And Mitochondrial Gene Expression by Contractile Activity In Skeletal Muscle," *The Journal Of Biological Chemistry 261*(1):376–380, 1986.

Williams, "Mitochondrial Gene Expression In Mammalian Striated Muscle," *The Journal Of Biological Chemistry 261*(26):12390–12394, 1986.

Anderson et al., "Mitochonrial Electron Transport Complexes Are Decreased In Skeletal Muscle In Type II Diabetes Mellitus," *Diabetes 48:* a259, 1999.

Ballinger et al., "Maternally Transmitted Diabetes And Deafness Associated With A 10.4 KB Mitochondrial DNA Deletion," *Nature Genetics 1:* 11–15, Apr. 1992.

Brignone et al., "Modified Oscillation Behaviour And Decreased D–3–Hydroxybutyrate Dehydrogenase Activity In Diabetic Rat Liver Mitochondria," *Archives of Biochemistry and Biophysics 214*(2): 581–588, Apr. 1982.

Gerbitz et al., "Mitochondria And Diabetes. Genetic, Biochemical, And Clinical Implications Of The Cellulat Energy Ciruit," *Diabetes 45*(2): 113–126, Feb. 1996.

Mathews et al., "A Point Mutation In The Mitochondrial DNA Of Diabetes–Prone BHE/cdb Rats," *FASEB Journal 9:* 1638–1642, 1995.

Van Den Ouweland et al., "Mutation In Mitochondrial tRNA$^{Leu(UUR)}$ Gene In A Large Pedigree With Maternally Transmitted Type II Diabetes Mellitus And Deafness," *Nature Genetics 1*(5): 368–371, Aug. 1992.

Su et al., "Selective Reduction Of Creatine Kinase Subunit mRNAs In Striated Muscle Of Diabetic Rats," *American Journal of Physiology 263:* e310–e316, 1992.

Vialettes et al., "Extra–Pancreatic Manifestations In Diabetes Secondary To Mitochrondrial DNA Point Mutation Within The tRNA$^{Leu(UUR)}$ Gene," *Diabetes Care 18*(7): 1023–1028, Jul. 1995.

Anderson; Drug Dev. Research, V. 46, No. 4; p67–79. (Abstract), Jan. 1999.*

Antonettie et al; J. Clin. Invest., V. 95, p1383–1388, 1995.*

Sepehrina et al; "Amer. J. Med. Genetics", V.56(2), p198–202, Mar. 1995.*

* cited by examiner

INDICATORS OF ALTERED MITOCHONDRIAL FUNCTION IN PREDICTIVE METHODS FOR DETERMINING RISK OF TYPE 2 DIABETES MELLITUS

CROSS-REFERENCE TO RELATED APPLICATION

This application is a continuation of pending U.S. patent application Ser. No. 09/303,816, filed Apr. 30, 1999.

TECHNICAL FIELD

The present invention relates generally to diabetes mellitus, and in particular to compositions and methods for the diagnosis, prognosis and treatment of type 2 diabetes.

BACKGROUND OF THE INVENTION

Type 2 diabetes mellitus, or "late onset" diabetes, is a common, degenerative disease affecting 5 to 10 percent of the population in developed countries. The propensity for developing type 2 diabetes mellitus ("type 2 DM") is reportedly maternally inherited, suggesting a mitochondrial genetic involvement. (Alcolado, J. C. and Alcolado, R., *Br. Med. J.* 302:1178–1180 (1991); Reny, S. L., *International J. Epidem.* 23:886–890 (1994)). Diabetes is a heterogeneous disorder with a strong genetic component; monozygotic twins are highly concordant and there is a high incidence of the disease among first degree relatives of affected individuals.

Current pharmacological therapies for type 2 DM include injected insulin, and oral agents that are designed to lower blood glucose levels. Currently available oral agents include (i) the sulfonylureas, which act by enhancing the sensitivity of the pancreatic beta cell to glucose, thereby increasing insulin secretion in response to a given glucose load; (ii) the biguanides, which improve glucose disposal rates and inhibit hepatic glucose output: (iii) the thiazolidinediones, which improve peripheral insulin sensitivity through interaction with nuclear peroxisome proliferator-activated receptors (PPAR, see, e.g., Spiegelman. 1998 *Diabetes* 47:507–514; Schoonjans et al., 1997 *Curr. Opin. Lipidol.* 8:159–166; Staels et al., 1997 *Biochimie* 79:95–99), (iv) repaglinide, which enhances insulin secretion through interaction with ATP-dependent potassium channels; and (v) acarbose, which decreases intestinal absorption of carbohydrates.

At the cellular level, the degenerative phenotype that may be characteristic of late onset diabetes mellitus includes indicators of altered mitochondrial respiratory function, for example impaired insulin secretion, decreased ATP synthesis and increased levels of reactive oxygen species. Studies have shown that type 2 DM may be preceded by or associated with certain related disorders. For example, it is estimated that forty million individuals in the U.S. suffer from impaired glucose tolerance (IGT). Following a glucose load, ciruculating glucose concentrations in IGT patients rise to higher levels, and return to baseline levels more slowly, than in unaffected individuals. A small percentage of IGT individuals (5–10%) progress to non-insulin dependent diabetes (NIDDM) each year. This form of diabetes mellitus, type 2 DM, is associated with decreased release of insulin by pancreatic beta cells and a decreased end-organ response to insulin. Other symptoms of diabetes mellitus and conditions that precede or are associated with diabetes mellitus include obesity, vascular pathologies, peripheral and sensory neuropathies and blindness.

It is clear that none of the current pharmacological therapies corrects the underlying biochemical defect in type 2 DM. Neither do any of these currently available treatments improve all of the physiological abnormalities in type 2 DM such as impaired insulin secretion, insulin resistance and/or excessive hepatic glucose output. In addition, treatment failures are common with these agents, such that multi-drug therapy is frequently necessary.

Due to the strong genetic component of diabetes mellitus, the nuclear genome has been the main focus of the search for causative genetic mutations. However, despite intense effort, nuclear genes that segregate with diabetes mellitus are rare and include, for example, mutations in the insulin gene, the insulin receptor gene and the glucokinase gene. By comparison, although a number of altered mitochondrial genes that segregate with diabetes mellitus have been reported (see generally e.g., PCT/US95/04063), relationships amongst mitochondrial and extramitochondrial factors that contribute to cellular respiratory and/or metabolic activities as they pertain to diabetes remain poorly understood.

Clearly there is a need for improved diagnostic methods for early detection of a risk for developing type 2 DM, and for better therapeutics that are targeted to correct biochemical and/or metabolic defects responsible for this disease, regardless of whether such a defect underlying altered mitochondrial function may have mitochondrial or extramnitochondrial origins. The present invention provides compositions and methods related to indicators of altered mitochondrial function that are useful for determining the risk and degree of progression of type 2 DM and for treating this disease, and offers other related advantages.

SUMMARY OF THE INVENTION

In one aspect the present invention provides a method for identifying a risk for Type 2 diabetes in a human subject, comprising comparing the level of at least one indicator of altered mitochondrial function in a biological sample from the subject with a control sample; and therefrom identifying the risk for Type 2 diabetes.

It is another aspect of the invention to provide a method for determining a degree of disease progression in a human subject having Type 2 diabetes, comprising: comparing the level of at least one indicator of altered mitochondrial function in each of first and second biological samples, the first and second biological samples being obtained from the subject at a first time point and a second time point, respectively; and therefrom determining the degree of progression of Type 2 diabetes. In yet another aspect the invention provides a method of identifying an agent suitable for treating a human subject suspected of being at risk for having type 2 diabetes, comprising: comparing the level of at least one indicator of altered mitochondrial function in one or more biological samples obtained from the subject in the presence and absence of a candidate agent; and therefrom determining the suitability of the candidate agent for treating type 2 diabetes. In still another aspect of the invention, there is provided a method of determining the suitability of an agent for treating a subject suspected of being at risk for having type 2 diabetes, comprising: comparing the level of at least one indicator of altered mitochondrial function in a biological sample obtained from the subject before and after administering to the subject a candidate agent; and therefrom determining the suitability of the candidate agent for treating type 2 diabetes.

Turning to another aspect, the invention provides a method of determining the suitability of an agent for treating a human subject suspected of being at risk for having type 2 diabetes, comprising comparing the level of at least one indicator of altered mitochondrial function in at least one biological sample obtained from a plurality of subjects before and after administering to each of the subjects a candidate agent; and therefrom determining the suitability of the candidate agent for treating type 2 diabetes.

It is another aspect of the present invention to provide a method of stratifying human subjects according to type 2 diabetes subtypes, comprising comparing the level of at least one indicator of altered mitochondrial function in at least one biological sample obtained from each of a plurality of subjects; and therefrom stratifying the subjects according to type 2 diabetes subtype. In yet another aspect the invention provides a method of stratifying human subjects according to type 2 diabetes subtypes, comprising: comparing the level of at least one indicator of altered mitochondrial function in a biological sample obtained from each of a plurality of subjects before and after administering to each of the subjects a candidate agent; and therefrom stratifying the subjects according to type 2 diabetes subtype.

According to certain embodiments within any of the above aspects of the invention, the indicator of altered mitochondrial function is a mitochondrial electron transport chain enzyme. In certain embodiments the step of comparing comprises measuring electron transport chain enzyme catalytic activity. In certain embodiments the step of measuring comprises determining enzyme activity per mitochondrion in the sample. In certain embodiments the step of measuring comprises determining enzyvme activity per unit of protein in the sample. In certain embodiments the step of comparing comprises measuring electron transport chain enzyme quantity. In certain embodiments the step of measuring comprises determining enzyme quantity per mitochondrion in the sample. In certain embodiments the step of measuring comprises determining enzyme quantity per unit of protein in the sample. In certain embodiments the mitochondrial electron transport chain enzyme comprises at least one subunit of mitochondrial complex I. In certain embodiments the mitochondrial electron transport chain enzyme comprises at least one subunit of mitochondrial complex II. In certain embodiments the mitochondrial electron transport chain enzyme comprises at least one subunit of mitochondrial complex III. In certain embodiments the mitochondrial electron transport chain enzyme comprises at least one subunit of mitochondrial complex IV. In certain embodiments the at least one subunit of mitochondrial complex IV is COX1, COX2 or COX4. In certain embodiments the mitochondrial electron transport chain enzyme comprises at least one subunit of mitochondrial complex V. In certain embodiments the at least one subunit of mitochondrial complex V is ATP synthase subunit 8 or ATP synthase subunit 6.

According to certain other embodiments of the above aspects of the invention, the indicator of altered mitochondrial function is a mitochondrial matrix component. In certain embodiments the indicator of altered mitochondrial function is a mitochondrial membrane component. In certain embodiments the mitochondrial membrane component is a mitochondrial inner membrane component. In certain embodiments the mitochondrial membrane component is adenine nucleotide translocator (ANT), voltage dependent anion channel (VDAC), malate-aspartate shuttle, calcium uniporter, UCP-1, UCP-2, UCP-3, a hexokinase, a peripheral benzodiazepine receptor, a mitochondrial intermembrane creatine kinase, cyclophilin D, a Bcl-2 gene family encoded polypeptide, tricarboxylate carrier or dicarboxylate carrier.

In certain embodiments the indicator of altered mitochondrial function is a Krebs cycle enzyme. In certain embodiments the step of comparing comprises measuring Krebs cycle enzyme catalytic activity. In certain embodiments the step of measuring comprises determining enzyme activity per mitochondrion in the sample. In certain embodiments the step of measuring comprises determining enzyme activity per unit of protein in the sample. In certain embodiments the step of comparing comprises measuring Krebs cycle enzyme quantity. In certain embodiments the step of measuring comprises determining enzyme quantity per mitochondrion in the sample. In certain embodiments the step of measuring comprises determining enzyme quantity per unit of protein in the sample. In certain embodiments the Krebs cycle enzyme is citrate synthase. In certain embodiments the Krebs cycle enzyme is aconitase, isocitrate dehydrogenase, alpha-ketoglutarate dehydrogenase, succinyl-coenzyme A synthetase, succinate dehydrogenase, fumarase or malate dehydrogenase.

In certain other embodiments of the above aspects of the invention, the indicator of altered mitochondrial function is mitochondrial mass per cell in the sample. In certain embodiments mitochondrial mass is determined using a mitochondria selective agent. In certain embodiments mitochondrial mass is determined using nonylacridine orange. In certain embodiments mitochondrial mass is determined by morphometric analysis. In certain embodiments the indicator of altered mitochondrial function is the number of mitochondria per cell in the sample. In certain embodiments the step of comparing comprises measuring a mitochondrion selective reagent. In certain embodiments the mitochondrion selective reagent is fluorescent.

According to certain other embodiments of the above aspects of the invention, the indicator of altered mitochondrial function is a co-predictor of altered mitochondrial function comprising the amount of mitochondrial DNA per cell in the sample and the step of comparing further comprises comparing at least one additional indicator of altered mitochondrial function. In certain embodiments the step of comparing comprises measuring mitochondrial DNA by contacting a biological sample containing mitochondrial DNA with an oligonucleotide primer having a nucleotide sequence that is complementary to a sequence present in the mitochondrial DNA, under conditions and for a time sufficient to allow hybridization of the primer to the mitochondrial DNA; and detecting hybridization of the primer to the mitochondrial DNA, and therefrom quantifying the mitochondrial DNA. In certain embodiments the step of detecting comprises a technique that may be polymerase chain reaction, oligonucleotide primer extension assay, ligase chain reaction, or restriction fragment length polymorphism analysis. In certain embodiments the step of comparing comprises measuring mitochondrial DNA by contacting a sample containing amplified mitochondrial DNA with an oligonucleotide primer having a nucleotide sequence that is complementary to a sequence present in the amplified mitochondrial DNA, under conditions and for a time sufficient to allow hybridization of the primer to the mitochondrial DNA; and detecting hybridization of the primer to the mitochondrial DNA, and therefrom quantifying the mitochondrial DNA. In certain embodiments the step of detecting comprises a technique that may be polymerase chain reaction, oligonucleotide primer extension assay, ligase chain reaction, or restriction fragment length polymorphism analysis. In certain embodiments the mitochondrial DNA is amplified using a technique that may be polymerase chain reaction, transcriptional amplification systems or self-sustained sequence replication. In certain embodiments the step of comparing comprises measuring mitochondrial DNA by contacting a biological sample containing mitochondrial DNA with an oligonucleotide primer having a nucleotide sequence that is complementary to a sequence present in the mitochondrial DNA, under conditions and for a time sufficient to allow hybridization of the primer to the mitochondrial DNA; and detecting hybridization and extension of the primer to the mitochondrial DNA to produce a product, and therefrom quantifying the mitochondrial DNA. In certain embodiments the step of comparing comprises measuring mitochondrial DNA by contacting a sample containing amplified mitochondrial DNA with an oligonucleotide primer having a nucleotide sequence that is complementary to a sequence present in the amplified mitochondrial DNA, under conditions and for a time sufficient to allow hybridization of the primer to the mitochondrial DNA; and detecting hybridization and extension of the primer to the mitochondrial DNA to produce a product, and therefrom quantizing the mitochondrial DNA. In certain embodiments the mitochondrial DNA is amplified using a technique that may be polymerase chain reaction, transcriptional amplification systems or self-sustained sequence replication. In certain embodiments the amount of mitochondrial DNA in the sample is determined using an oligonucleotide primer extension assay.

In certain embodiments of any of the above aspects of the invention, the indicator of altered mitochondrial function is the amount of ATP per cell in the sample. In certain embodiments the step of comparing comprises measuring the amount of ATP per mitochondrion in the sample. In certain embodiments the step of comparing comprises measuring the amount of ATP per unit protein in the sample. In certain embodiments the step of comparing comprises measuring the amount of ATP per unit mitochondrial mass in the sample. In certain embodiments the step of comparing comprises measuring the amount of ATP per unit mitochondrial protein in the sample. In certain embodiments the indicator of altered mitochondrial function is the rate of ATP synthesis in the sample. In certain embodiments the indicator of altered mitochondrial function is an ATP biosynthesis factor. In certain embodiments the step of comparing comprises measuring ATP biosynthesis factor catalytic activity. In certain embodiments the step of measuring comprises determining ATP biosynthesis factor activity per mitochondrion in the sample.

In certain embodiments the step of measuring comprises determining ATP biosynthesis factor activity per unit mitochondrial mass in the sample. In certain embodiments the step of measuring comprises determining ATP biosynthesis factor activity per unit of protein in the sample. In certain embodiments the step of comparing comprises measuring ATP biosynthesis factor quantity. In certain embodiments the step of measuring comprises determining ATP biosynthesis factor quantity per mitochondrion in the sample. In certain embodiments the step of measuring comprises determining ATP biosynthesis factor quantity per unit of protein in the sample.

In certain embodiments of any of the above aspects of the present invention, the indicator of altered mitochondrial function is free radical production. In certain embodiments the indicator of altered mitochondrial function is reactive oxygen species, protein nitrosylation, protein carbonyl modification, DNA oxidation, mtDNA oxidation, protein oxidation, protein carbonyl modification, malondialdehyde adducts of proteins, a glycoxidation product, a lipoxidation product, 8'-OH-guanosine adducts or TBARS. In certain embodiments the indicator of altered mitochondrial function is reactive oxygen species. In certain embodiments the indicator of altered mitochondrial function is protein nitrosylation. In certain embodiments the indicator of altered mitochondrial function is DNA oxidation. In certain embodiments the indicator of altered mitochondrial function is mitochondrial DNA oxidation. In certain embodiments the indicator of altered mitochondrial function is protein carbonyl modification.

In yet other certain embodiments of any of the above aspects of the instant invention, the indicator of altered mitochondrial function is a cellular response to elevated intracellular calcium. In certain other embodiments the indicator of altered mitochondrial function is a cellular response to at least one apoptogen. In certain other embodiments the at least one indicator of altered mitochondrial function is a co-indicator of altered mitochondrial function and the step of comparing further comprises comparing at least one additional non-enzyme indicator of altered mitochondrial function. In certain embodiments the at least one additional non-enzyme indicator of altered mitochondrial function is a level of mitochondrial protein in the sample. In certain embodiments the co-indicator of altered mitochondrial function is citrate synthase, hexokinase II, cytochrome c oxidase, phosphofructokinase, glyceraldehyde phosphate dehydrogenase, glycogen phosphorylase, creatine kinase, NADH dehydrogenase, glycerol 3-phosphate dehydrogenase, triose phosphate dehydrogenase or malate dehydrogenase.

Turning to another aspect, the invention provides a method of treating a human patient having type 2 diabetes mellitus, comprising administering to the patient an agent that substantially restores to a normal level at least one indicator of altered mitochondrial function. In certain embodiments the indicator of altered mitochondrial function is a mitochondrial electron transport chain enzyme, a Krebs cycle enzyme, a mitochondrial matrix component, a mitochondrial membrane component or an ATP biosynthesis factor. In certain embodiments the indicator of altered mitochondrial function is mitochondrial number per cell or mitochondrial mass per cell. In certain embodiments the indicator of altered mitochondrial function is an ATP biosynthesis factor. In certain embodiments the indicator of altered mitochondrial function is the amount of ATP per mitochondrion, the amount of ATP per unit mitochondrial mass, the amount of ATP per unit protein or the amount of ATP per unit mitochondrial protein. In certain embodiments the indicator of altered mitochondrial function comprises free radical production. In certain embodiments the indicator of altered mitochondrial function comprises a cellular response to elevated intracellular calcium. In certain embodiments the at least one indicator of altered mitochondrial function is a co-indicator of altered mitochondrial function. In certain embodiments the co-indicator of altered mitochondrial function is citrate synthase, hexokinase II, cytochrome c oxidase, phosphofructokinase, glyceraldehyde phosphate dehydrogenase, glycogen phosphorylase, creatine kinase, NADH dehydrogenase, glycerol 3-phosphate dehydrogenase, triose phosphate dehydrogenase or malate dehydrogenase. In certain embodiments the at least one indicator of altered mitochondrial function is a co-predictor of altered mitochondrial function. In certain embodiments the co-predictor of altered mitochondrial function is an amount of mitochondrial DNA per cell in the patient.

These and other aspects of the present invention will become evident upon reference to the following detailed description and attached drawings. In addition, various references are set forth herein which describe in more detail certain aspects of this invention, and are therefore incorporated by reference in their entireties.

DETAILED DESCRIPTION OF THE INVENTION

Figure 1:
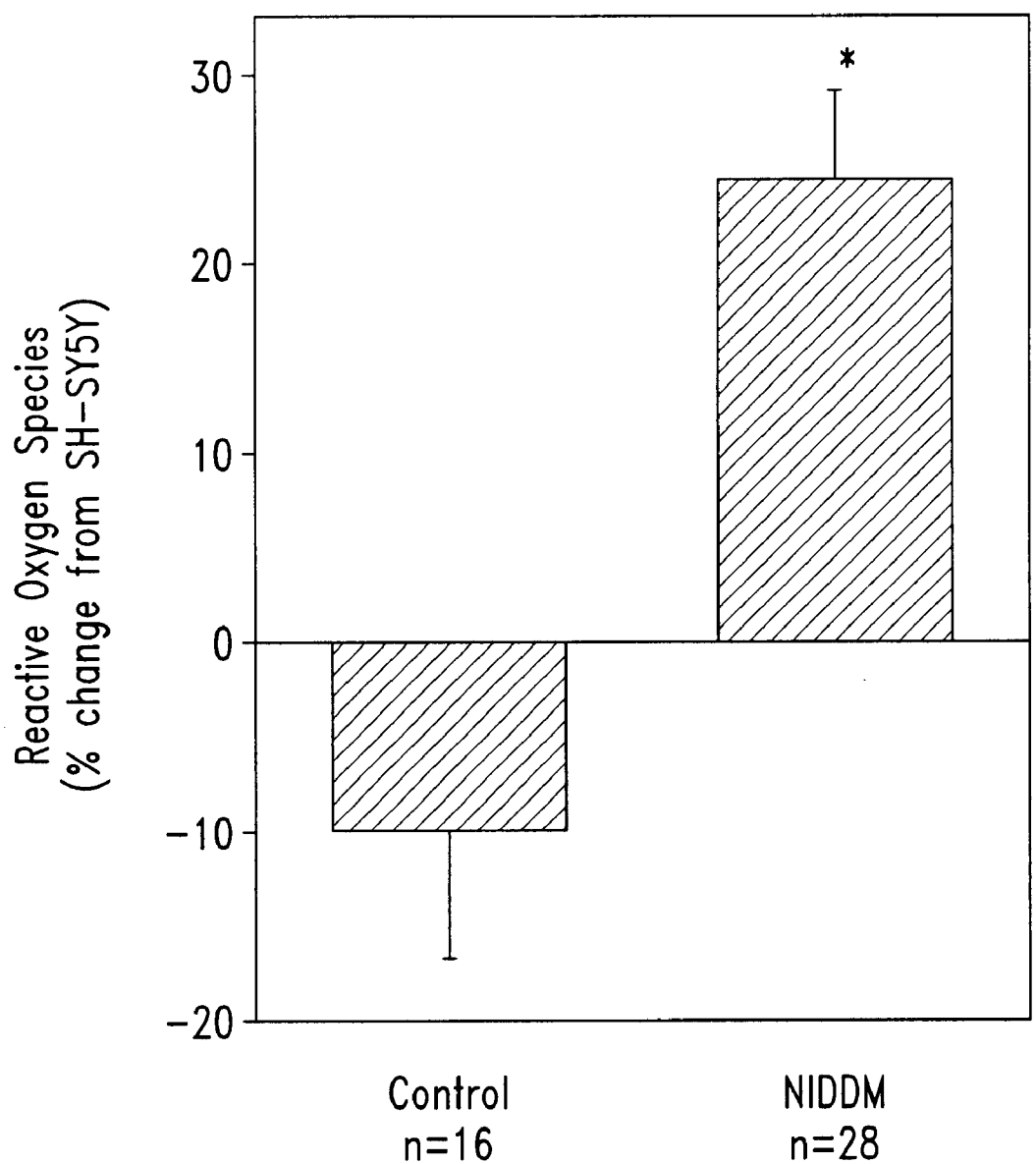
FIG. 1 shows detection of reactive oxygen species in cybrid cell lines produced using either mitochondria from a subject having type 2 DM or mitochondria from subjects known to be free of this disease.

The present invention provides compositions and methods that are useful in pre-symptomatic detection of type 2 DM and in the identification of therapeutics for treating type 2 DM.

The methods of the present invention pertain in part to the correlation of type 2 DM with an increased or decreased level of at least one indicator of altered mitochondrial function. In particular, according to the present invention, an "indicator of altered mitochondrial function" may be any detectable parameter that directly relates to a condition, process, pathway, dynamic structure, state or other activity involving mitochondria and that permits detection of altered mitochondrial function in a biological sample from a subject or biological source. The methods of the present invention thus pertain in part to such correlation where the indicator of altered mitochondrial function may be, for example, a mitochondrial enzyme, or other criteria as provided herein.

"Altered mitochondrial function" may refer to any condition or state, including those that accompany type 2 DM, where any structure or activity that is directly or indirectly related to a mitochondrial function has been changed in a statistically significant manner relative to a control or standard. Altered mitochondrial function may have its origin in extramitochondrial structures or events as well as in mitochondrial structures or events, in direct interactions between mitochondrial and extramitochondrial genes and/or their gene products, or in structural or functional changes that occur as the result of interactions between intermediates that may be formed as the result of such interactions, including metabolites, catabolites, substrates, precursors, cofactors and the like.

Additionally, altered mitochondrial function may include altered respirator, metabolic or other biochemical or biophysical activity in some or all cells of a biological source. As non-limiting examples, markedly impaired ETC activity may be related to altered mitochondrial function, as may be generation of increased ROS or defective oxidative phosphorylation. As further examples, altered mitochondrial membrane potential, induction of apoptotic pathways and formation of atypical chemical and biochemical crosslinked species within a cell, whether by enzymatic or non-enzymatic mechanisms, may all be regarded as indicative of altered mitochondrial function. These and other non-limiting examples of altered mitochondrial function are described in greater detail below.

Without wishing to be bound by theory, altered mitochondrial function characteristic of type 2 DM may also be related to loss of mitochondrial membrane electrochemical potential by mechanisms other than free radical oxidation, for example by defects in transmitochondrial membrane shuttles and transporters such as the adenine nucleotide transporter or the malate-aspartate shuttle, by intracellular calcium flux, by defects in ATP biosynthesis, by impaired association with porin of hexokinases or other enzymes or by other events. Such collapse of mitochondrial inner membrane potential may result from direct or indirect effects of mitochondrial genes, gene products or related downstream mediator molecules and/or extramitochondrial genes, gene products or related downstream mediators, or from other known or unknown causes.

In certain embodiments of the present invention, type 2 DM may be correlated with an increased or decreased level of at least one "co-indicator of altered mitochondrial function". A co-indicator of altered mitochondrial function refers to an indicator of altered mitochondrial function, as provided herein, that is determined concurrently with at least one additional and distinct non-enzyme indicator of altered mitochondrial function. For example, a co-indicator of altered mitochondrial function may refer to an indicator of altered mitochondrial function as provided herein, which is quantified in relation to an additional non-enzyme indicator of altered mitochondrial function. For instance, a co-indicator of altered mitochondrial function may be an enzyme determined on the basis of its level per unit mitochondrial protein in a sample (e.g. mitochondrial protein in the sample may be the additional non-enzyme indicator of altered mitochondrial function), but the invention need not be so limited.

By way of background, functional mitochondria contain gene products encoded by mitochondrial genes situated in mitochondrial DNA (mtDNA) and by extramitochondrial genes (e.g., nuclear genes) not situated in the circular mitochondrial genome. The 16.5 kb mtDNA encodes 22 tRNAs, two ribosomal RNAs (rRNA) and 13 enzymes of the electron transport chain (ETC), the elaborate multi-complex mitochondrial assembly where, for example, respiratory oxidative phosphorylation takes place. The overwhelming majority of mitochondrial structural and functional proteins are encoded by extramitochondrial, and in most cases presumably nuclear, genes. Accordingly, mitochondrial and extramitochondrial genes may interact directly, or indirectly via gene products and their downstream intermediates, including metabolites, catabolites, substrates, precursors, cofactors and the like. Alterations in mitochondrial function, for example impaired electron transport activity, defective oxidative phosphorylation or increased free radical production, may therefore arise as the result of defective mtDNA, defective extramitochondrial DNA, defective mitochondrial or extramitochondrial gene products, defective downstream intermediates or a combination of these and other factors.

In the most highly preferred embodiments of the invention, an enzyme is the indicator of altered mitochondrial function as provided herein. The enzyme may be a mitochondrial enzyme, which may further be an ETC enzyme or a Krebs cycle enzyme. The enzyme may also be an ATP biosynthesis factor, which may include an ETC enzyme and/or a Krebs cycle enzyme, or other enzymes or cellular components related to ATP production as provided herein. A "non-enzyme" refers to an indicator of altered mitochondrial function that is not an enzyme (i.e., that is not a mitochondrial enzyme or an ATP biosynthesis factor as provided herein). In certain other preferred embodiments, an enzyme is a co-indicator of altered mitochondrial function. The following enzymes may not be indicators of altered mitochondrial function according to the present invention, but may be co-indicators of altered mitochondrial function as provided herein: citrate synthase (EC 4.1.3.7), hexokinase II (EC 2.7.1.1; see, e.g., Kruszynska et al. 1998), cytochrome c oxidase (EC 1.9.3.1), phosphofructokinase (EC 2.7.1.11), glyceraldehyde phosphate dehydrogenase (EC 1.2.1.12), glycogen phosphorylase (EC 2.4.1.1) creatine kinase (EC 2.7.3.2), NADH dehydrogenase (EC 1.6.5.3), glycerol 3-phosphate dehydrogenase (EC 1.1.1.8), triose phosphate dehydrogenase (EC 1.2.1.12) and malate dehydrogenase (EC 1.1.1.37).

In other highly preferred embodiments, the indicator of altered mitochondrial function is any ATP biosynthesis factor as described below. In other preferred embodiments, the indicator is ATP production. In other preferred embodiments, the indicator of altered mitochondrial function may be mitochondrial mass or mitochondrial number. According to the present invention, mitochondrial DNA content may not be an indicator of altered mitochondrial function but may be a co-predictor of altered mitochondrial function or a co-indicator of altered mitochondrial function, as provided herein. In other preferred embodiments the indicator of altered mitochondrial function may be free radical production, a cellular response to elevated intracellular calcium or a cellular response to an apoptogen.

INDICATORS OF ALTERED MITOCHONDRIAL FUNCTION THAT ARE ENZYMES

Certain aspects of the invention are directed to a method for identifying a risk for Type 2 diabetes in a subject comprising comparing the level of at least one indicator of altered mitochondrial function in a biological sample with a control sample, wherein the indicator of altered mitochondrial function is an enzyme. As provided herein, in certain most highly preferred embodiments, such an enzyme may be a mitochondrial enzyme or an ATP biosynthesis factor that is an enzyme, for example an ETC enzyme or a Krebs cycle enzyme.

Reference herein to "enzyme quantity", "enzyme catalytic activity" or "enzyme expression level" is meant to include a reference to any of a mitochondrial enzyme quantity, activity or expression level or an ATP biosynthesis factor quantity, activity or expression level; either of which may further include, for example, an ETC enzyme quantity, activity or expression level or a Krebs cycle enzyme quantity, activity or expression level. In the most preferred embodiments of the invention, an enzyme is a natural or recombinant protein or polypeptide that has enzyme catalytic activity as provided herein. Such an enzyme may be, by way of non-limiting examples, an enzyme, a holoenzyme, an enzyme complex, an enzyme subunit, an enzyme fragment, derivative or analog or the like, including a truncated, processed or cleaved enzyme.

A "mitochondrial enzyme" that may be an indicator of altered mitochondrial function as provided herein refers to a mitochondrial molecular component that has enzyme catalytic activity and/or functions as an enzyme cofactor capable of influencing enzyme catalytic activity. As used herein, mitochondria are comprised of "mitochondrial molecular components", which may be a protein, polypeptide, peptide, amino acid, or derivative thereof; a lipid, fatty acid or the like, or derivative thereof, a carbohydrate, saccharide or the like or derivative thereof, a nucleic acid, nucleotide, nucleoside, purine, pyrimidine or related molecule, or derivative thereof, or the like; or any covalently or non-covalently complexed combination of these components, or any other biological molecule that is a stable or transient constituent of a mitochondrion.

A mitochondrial enzyme that may be an indicator of altered mitochondrial function or a co-indicator of altered mitochondrial function as provided herein, or an ATP biosynthesis factor that may be an indicator of altered mitochondrial function as provided herein, may comprise an ETC enzyme, which refers to any mitochondrial molecular component that is a mitochondrial enzyme component of the mitochondrial electron transport chain (ETC) complex associated with the inner mitochondrial membrane and mitochondrial matrix. An ETC enzyme may include any of the multiple ETC subunit polypeptides encoded by mitochondrial and nuclear genes. The ETC is typically described as comprising complex I (NADH:ubiquinone reductase), complex II (succinate dehydrogenase), complex III (ubiquinone, cytochrome c oxidoreductase), complex IV (cytochrome c oxidase) and complex V (mitochondrial ATP synthetase), where each complex includes multiple polypeptides and cofactors (for review see, e.g. Walker et al., 1995 *Meths. Enzymol.* 260:14; Ernster et al., 1981 *J. Cell Biol.* 91:227s–255s, and references cited therein).

A mitochondrial enzyme that may be an indicator of altered mitochondrial function as provided herein, or an ATP biosynthesis factor that may be an indicator of altered mitochondrial function as provided herein, may also comprise a Krebs cycle enzyme, which includes mitochondrial molecular components that mediate the series of biochemical/bioenergetic reactions also known as the citric acid cycle or the tricarboxylic acid cycle (see, e.g., Lehninger, Biochemistry, 1975 Worth Publishers, NY; Voet and Voet, Biochemistry, 1990 John Wiley & Sons, NY; Mathews and van Holde, Biochemistry, 1990 Benjamin Cummings, Menlo Park, Calif.). Krebs cycle enzymes include subunits and cofactors of citrate synthase, aconitase, isocitrate dehydrogenase, the α-ketoglutarate dehydrogenase complex, succinyl CoA synthetase, succinate dehydrogenase, fumarase and malate dehydrogenase. Krebs cycle enzymes further include enzymes and cofactors that are functionally linked to the reactions of the Krebs cycle, such as, for example, nicotinamide adenine dinucleotide, coenzyme A, thiamine pyrophosphate, lipoamide, guanosine diphosphate, flavin adenine dinucloetide and nucleoside diphosphokinase.

The methods of the present invention also pertain in part to the correlation of type 2 DM with an indicator of altered mitochondrial function that may be an ATP biosynthesis factor, an altered amount of ATP or an altered amount of ATP production. For example, decreased mitochondrial ATP biosynthesis may be an indicator of altered mitochondrial function from which a risk for type 2 DM may be identified.

An "ATP biosynthesis factor" refers to any naturally occurring cellular component that contributes to the efficiency of ATP production in mitochondria. Such a cellular component may be a protein, polypeptide, peptide, amino acid, or derivative thereof; a lipid, fatty acid or the like, or derivative thereof; a carbohydrate, saccharide or the like or derivative thereof, a nucleic acid, nucleotide, nucleoside, purine, pyrimidine or related molecule, or derivative thereof, or the like. An ATP biosynthesis factor includes at least the components of the ETC and of the Krebs cycle (see, e.g., Lehninger, Biochemistry, 1975 Worth Publishers, NY; Voet and Voet, Biochemistry, 1990 John Wiley & Sons, NY; Mathews and van Holde, Biochemistry, 1990 Benjamin Cummings, Menlo Park, Calif.) and any protein, enzyme or other cellular component that participates in ATP synthesis, regardless of whether such ATP biosynthesis factor is the product of a nuclear gene or of an extranuclear gene (e.g, a mitochondrial gene). Participation in ATP synthesis may include, but need not be limited to, catalysis of any reaction related to ATP synthesis, transmembrane import and/or export of ATP or of an enzyme cofactor, transcription of a gene encoding a mitochondrial enzyme and/or translation of such a gene transcript.

Compositions and methods for determining whether a cellular component is an ATP biosynthesis factor are well known in the art, and include methods for determining ATP production (including determination of the rate of ATP production in a sample) and methods for quantifying ATP itself. The contribution of an ATP biosynthesis factor to ATP production can be determined, for example, using an isolated ATP biosynthesis factor that is added to cells or to a cell-free system. The ATP biosynthesis factor may directly or indirectly mediate a step or steps in a biosynthetic pathway that influences ATP production. For example, an ATP biosynthesis factor may be an enzyme that catalyzes a particular chemical reaction leading to ATP production. As another example, an ATP biosynthesis factor may be a cofactor that enhances the efficiency of such an enzyme. As another example, an ATP biosynthesis factor may be an exogenous genetic element introduced into a cell or a cell-free system that directly or indirectly affects an ATP biosynthetic pathway. Those having ordinary skill in the art are readily able to compare ATP production by an ATP biosynthetic pathway in the presence and absence of a candidate ATP biosynthesis factor. Routine determination of ATP production may be accomplished using any known method for quantitative ATP detection, for example by way of illustration and not limitation, by differential extraction from a sample optionally including chromatographic isolation; by spectrophotometry; by quantification of labeled ATP recovered from a sample contacted with a suitable form of a detectably labeled ATP precursor molecule such as, for example, $^{32}P$; by quantification of an enzyme activity associated with ATP synthesis or degradation; or by other techniques that are known in the art. Accordingly, in certain embodiments of the present invention, the amount of ATP in a biological sample or the production of ATP (including the rate of ATP production) in a biological sample may be an indicator of altered mitochondrial function. In one embodiment, for instance, ATP may be quantified by measuring luminescence of luciferase catalyzed oxidation of D-luciferin, an ATP dependent process.

"Enzyme catalytic activity" refers to any function performed by a particular enzyme or category of enzymes that is directed to one or more particular cellular function(s). For example, "ATP biosynthesis factor catalytic activity" refers to any function performed by an ATP biosynthesis factor as provided herein that contributes to the production of ATP. Typically, enzyme catalytic activity is manifested as facilitation of a chemical reaction by a particular enzyme, for instance an enzyme that is an ATP biosynthesis factor, wherein at least one enzyme substrate or reactant is covalently modified to form a product. For example, enzyme catalytic activity may result in a substrate or reactant being modified by formation or cleavage of a covalent chemical bond, but the invention need not be so limited. Various methods of measuring enzyme catalytic activity are known to those having ordinary skill in the art and depend on the particular activity to be determined.

For many enzymes, including mitochondrial enzymes or enzymes that are ATP biosynthesis factors as provided herein, quantitative criteria for enzyme catalytic activity are well established. These criteria include, for example, activity that may be defined by international units (IU), by enzyme turnover number, by catalytic rate constant ($K_{cat}$), by Michaelis-Menten constant ($K_m$), by specific activity or by any other enzymological method known in the art for measuring a level of at least one enzyme catalytic activity. Specific activity of a mitochondrial enzyme, such as an ATP biosynthesis factor, may be expressed as units of substrate detectably converted to product per unit time and, optionally, further per unit sample mass (e.g., per unit protein or per unit mitochondrial mass).

In certain preferred embodiments of the invention, enzyme catalytic activity may be expressed as units of substrate detectably converted by an enzyme to a product per unit time per unit total protein in a sample. In certain particularly preferred embodiments, enzyme catalytic activity may be expressed as units of substrate detectably converted by an enzyme to product per unit time per unit mitochondrial mass in a sample. In certain highly preferred embodiments, enzyme catalytic activity may be expressed as units of substrate detectably converted by an enzyme to product per unit time per unit mitochondrial protein mass in a sample. Products of enzyme catalytic activity may be detected by suitable methods that will depend on the quantity and physicochemical properties of the particular product. Thus, detection may be, for example by way of illustration and not limitation, by radiometric, colorimetric, spectrophotometric, fluorimetric, immunometric or mass spectrometric procedures, or by other suitable means that will be readily apparent to a person having ordinarn skill in the art.

In certain embodiments of the invention, detection of a product of enzyme catalytic activity may be accomplished directly, and in certain other embodiments detection of a product may be accomplished by introduction of a detectable reporter moiety or label into a substrate or reactant such as a marker enzyme, dye, radionuclide, luminescent group, fluorescent group or biotin, or the like. The amount of such a label that is present as unreacted substrate and/or as reaction product, following a reaction to assay enzyme catalytic activity, is then determined using a method appropriate for the specific detectable reporter moiety or label. For radioactive groups, radionuclide decay monitoring, scintillation counting, scintillation proximity assays (SPA) or autoradiographic methods are generally appropriate. For immunometric measurements, suitably labeled antibodies may be prepared including, for example, those labeled with radionuclides, with fluorophores, with affinity tags, with biotin or biotin mimetic sequences or those prepared as antibody-enzyme conjugates (see, e.g., Weir, D. M., *Handbook of Experimental Immunology*, 1986, Blackwell Scientific, Boston; Scouten, W. H., *Methods in Enzymology* 135:30–65, 1987; Harlow and Lane, *Antibodies: A Laboratory Manual*, Cold Spring Harbor Laboratory, 1988; Haugland, 1996 *Handbook of Fluorescent Probes and Research Chemicals—Sixth Ed.*, Molecular Probes, Eugene, Oreg.; Scopes, R. K., *Protein Purification: Principles and Practice*, 1987, Springer-Verlag, N.Y.; Hermanson. G. T. et al., *Immobilized Affinity Ligand Techniques*, 1992. Academic Press, Inc., NY; Luo et al., 1998 *J. Biotechnol*. 65:225 and references cited therein). Spectroscopic methods may be used to detect dyes (including, for example, colorimetric products of enzyme reactions), luminescent groups and fluorescent groups. Biotin may be detected using avidin or streptavidin, coupled to a different reporter group (commonly a radioactive or fluorescent group or an enzyme). Enzyme reporter groups may generally be detected by the addition of substrate (generally for a specific period of time), followed by spectroscopic, spectrophotometric or other analysis of the reaction products. Standards and standard additions may be used to determine the level of enzyme catalytic activity in a sample, using well known techniques.

As noted above, enzyme catalytic activity of an ATP biosynthesis factor may further include other functional activities that lead to ATP production, beyond those involving covalent alteration of a substrate or reactant. For example by way of illustration and not limitation, an ATP biosynthesis factor that is an enzyme may refer to a transmembrane transporter molecule that, through its enzyme catalytic activity, facilitates the movement of metabolites between cellular compartments. Such metabolites may be ATP or other cellular components involved in ATP synthesis, such as gene products and their downstream intermediates, including metabolites, catabolites, substrates, precursors, cofactors and the like. As another non-limiting example, an ATP biosynthesis factor that is an enzyme may through its enzyme catalytic activity, transiently bind to a cellular component involved in ATP synthesis in a manner that promotes ATP synthesis. Such a binding event may, for instance, deliver the cellular component to another enzyme involved in ATP synthesis and/or may alter the conformation of the cellular component in a manner that promotes ATP synthesis. Further to this example, such conformational alteration may be part of a signal transduction pathway, an allosteric activation pathway, a transcriptional activation pathway or the like, where an interaction between cellular components leads to ATP production.

Thus, according to the present invention, an ATP biosynthesis factor may include, for example, a mitochondrial membrane protein. Suitable mitochondrial membrane proteins include such mitochondrial components as the adenine nucleotide transporter (ANT; e.g., Fiore et al., 1998 *Biochimie* 80:137; Klingenberg 1985 *Ann. N.Y. Acad. Sci.* 456:279), the voltage dependent anion channel (VDAC, also referred to as porin; e.g., Manella, 1997 *J. Bioenergetics Biomembr.* 29:525), the malate-aspartate shuttle, the mitochondrial calcium uniporter (e.g., Litsky et al., 1997 *Biochem.* 36:7071), uncoupling proteins (UCP-1, -2, -3; see e.g., Jezek et al., 1998 *Int. J. Biochem. Cell Biol.* 30:1163), a hexokinase, a peripheral benzodiazepine receptor, a mitochondrial intermembrane creatine kinase, cyclophilin D, a Bcl-2 gene family encoded polypeptide, the tricarboxylate carrier (e.g., Iocobazzi et al., 1996 Biochim. Biophys. Acta 1284:9; Bisaccia et al., 1990 Biochim. Biophys. Acta 1019:250) and the dicarboxylate carrier (e.g., Fiermonte et al., 1998 *J. Biol. Chem.* 273:24754; Indiveri et al., 1993 *Biochim. Biophys. Acta* 1143:310; for a general review of mitochondrial membrane transporters, see, e.g., Zonatti et al., 1994 *J. Bioenergetics Biomembr.* 26:543 and references cited therein).

"Enzyme quantity" as used herein refers to an amount of an enzyme including mitochondrial enzymes or enzymes that are ATP biosynthesis factors as provided herein, or of another ATP biosynthesis factor, that is present, i.e., the physical presence of an enzyme or ATP biosynthesis factor selected as an indicator of altered mitochondrial function, irrespective of enzyme catalytic activity. Depending on the physicochemical properties of a particular enzyme or ATP biosynthesis factor, the preferred method for determining the enzyme quantity will vary. In the most highly preferred embodiments of the invention, determination of enzyme quantity will involve quantitative determination of the level of a protein or polypeptide using routine methods in protein chemistry with which those having skill in the art will be readily familiar, for example by way of illustration and not limitation, those described in greater detail below.

Accordingly, determination of enzyme quantity may be by any suitable method known in the art for quantifying a particular cellular component that is an enzyme or an ATP biosynthesis factor as provided herein, and that in preferred embodiments is a protein or polypeptide. Depending on the nature and physicochemical properties of the enzyme or ATP biosynthesis factor, determination of enzyme quantity may be by densitometric, mass spectrometric, spectrophotometric, fluorimetric, immunometric, chromatographic, electrochemical or any other means of quantitatively detecting a particular cellular component. Methods for determining enzyme quantity also include methods described above that are useful for detecting products of enzyme catalytic activity, including those measuring enzyme quantity directly and those measuring a detectable label or reporter moiety. In certain preferred embodiments of the invention, enzyme quantity is determined by immunometric measurement of an isolated enzyme or ATP biosynthesis factor. In certain preferred embodiments of the invention, these and other immunological and immunochemical techniques for quantitative determination of biomolecules such as an enzyme or ATP biosynthesis factor may be employed using a variety of assay formats known to those of ordinary skill in the art, including but not limited to enzyme linked immunosorbent assay (ELISA), radioimmunoassay (RIA), immunofluorimetry, immunoprecipitation, equilibrium dialysis, immunodiffusion and other techniques. (See, e.g., Harlow and Lane, *Antibodies: A Laboratory Manual*, Cold Spring Harbor Laboratory, 1988; Weir, D. M., *Handbook of Experimental Immunology*, 1986, Blackwell Scientific, Boston.) For example, the assay may be performed in a Western blot format, wherein a preparation comprising proteins from a biological sample is submitted to gel electrophoresis, transferred to a suitable membrane and allowed to react with an antibody specific for an enzyme or an ATP biosynthesis factor that is a protein or polypeptide. The presence of the antibody on the membrane may then be detected using a suitable detection reagent, as is well known in the art and described above.

In certain embodiments of the invention, an indicator (or co-indicator) of altered mitochondrial function including, for example, an enzyme as provided herein, may be present in isolated form. The term "isolated" means that a material is removed from its original environment (e.g., the natural environment if it is naturally occurring). For example, a naturally occurring polypeptide present in a living animal is not isolated, but the same polypeptide, separated from some or all of the co-existing materials in the natural system, is isolated. Such polypeptides could be part of a composition, and still be isolated in that such composition is not part of its natural environment.

Affinity techniques are particularly useful in the context of isolating an enzyme or an ATP biosynthesis factor protein or polypeptide for use according to the methods of the present invention, and may include any method that exploits a specific binding interaction involving an enzyme or an ATP biosynthesis factor to effect a separation. For example, because an enzyme or an ATP biosynthesis factor protein or polypeptide may contain covalently attached oligosaccharide moieties, an affinity technique such as binding of the enzyme (or ATP biosynthesis factor) to a suitable immobilized lectin under conditions that permit carbohydrate binding by the lectin may be a particularly useful affinity technique.

Other useful affinity techniques include immunological techniques for isolating and/or detecting a specific protein or polypeptide antigen (e.g., an enzyme or ATP biosynthesis factor), which techniques rely on specific binding interaction between antibody combining sites for antigen and antigenic determinants present on the factor. Binding of an antibody or other affinity reagent to an antigen is "specific" where the binding interaction involves a $K_a$ of greater than or equal to about $10^4$ $M^{-1}$, preferably of greater than or equal to about $10^5$ $M^{-1}$, more preferably of greater than or equal to about $10^6$ $M^{-1}$ and still more preferably of greater than or equal to about $10^7$ $M^{-1}$. Affinities of binding partners or antibodies can be readily determined using conventional techniques, for example those described by Scatchard et al., *Ann. N.Y. Acad. Sci.* 51:660 (1949).

Immunological techniques include, but need not be limited to, immunoaffinity chromatography, immunoprecipitation, solid phase immunoadsorption or other immunoaffinity methods. For these and other useful affinity techniques, see, for example, Scopes, R. K., *Protein Purification: Principles and Practice*, 1987, Springer-Verlag, NY; Weir, D. M., *Handbook of Experimental Immunology*, 1986, Blackwell Scientific, Boston; and Hermanson, G. T. et al., *Immobilized Affinity Ligand Techniques*, 1992, Academic Press, Inc., California; which are hereby incorporated by reference in their entireties, for details regarding techniques for isolating and characterizing complexes, including affinity techniques.

As noted above, an indicator of altered mitochondrial function can be a protein or polypeptide, for example an enzyme or an ATP biosynthesis factor. The protein or polypeptide may be an unmodified polypeptide or may be a polypeptide that has been posttranslationally modified, for example by glycosylation, phosphorylation, fatty acylation including glycosylphosphatidylinositol anchor modification or the like, phospholipase cleavage such as phosphatidylinositol-specific phospholipase c mediated hydrolysis or the like, protease cleavage, dephosphorylation or any other type of protein posttranslational modification such as a modification invoiving formation or cleavage of a covalent chemical bond.

INDICATORS OF ALTERED MITOCHONDRIAL FUNCTION THAT ARE MITOCHONDRIAL MASS, MITOCHONDRIAL VOLUME OR MITOCHONDRIAL NUMBER

According to certain embodiments, the invention is directed to a method for identifying a risk for Type 2 diabetes in a subject comprising comparing the level of at least one indicator of altered mitochondrial function in a biological sample with a control sample, wherein the indicator of altered mitochondrial function is at least one of mitochondrial mass, mitochondrial volume or mitochondrial number.

Methods for quantifying mitochondrial mass, volume and/or mitochondrial number are known in the art, and may include, for example, quantitative staining of a representative biological sample. Typically, quantitative staining of mitochondrial may be performed using organelle-selective probes or dyes, including but not limited to mitochondrion selective reagents such as fluorescent dyes that bind to mitochondrial molecular components (e.g, nonylacridine orange, MtitoTrackers™) or potentiometric dyes that accumulate in mitochondria as a function of mitochondrial inner membrane electrochemical potential (see, e.g., Haugland, 1996 *Handbook of Fluorescent Probes and Research Chemicals—Sixth Ed.*, Molecular Probes, Eugene, Oreg.).

As another example, mitochondrial mass, volume and/or number may be quantified by morphometric analysis (e.g., Cruz-Orive et al., 1990 *Am. J. Physiol.* 258:L148; Schwerzmann et al., 1986 *J. Cell Biol.* 102:97). These or any other means known in the art for quantifying mitochondrial mass, volume and/or mitochondrial number in a sample are within the contemplated scope of the invention. For example, the use of such quantitative determinations for purposes of calculating mitochondrial density is contemplated and is not intended to be limiting. In certain highly preferred embodiments, mitochondrial protein mass in a sample is determined using well known procedures. For example, a person having ordinary skill in the art can readily prepare an isolated mitochondrial fraction from a biological sample using established cell fractionation techniques, and therefrom determine protein content using any of a number of protein quantification methodologies well known in the art.

CO-PREDICTORS OF ALTERED MITOCHONDRIAL FUNCTION THAT INCLUDE MITOCHONDRIAL DNA CONTENT

According to certain other particular embodiments, the invention contemplates a "co-predictor" of altered mitochondrial function, which refers to an indicator of altered mitochondrial function, as provided herein, that is determined concurrently with at least one additional and distinct indicator of altered mitochondrial function, which may be an indicator or co-indicator of altered mitochondrial function as described above. In preferred embodiments, a co-predictor of altered mitochondrial function may be mitochondrial DNA content in a biological sample, and in particularly preferred embodiments the co-predictor of altered mitochondrial function comprises the amount of mitochondrial DNA per cell in the sample, and in other particularly preferred embodiments the co-predictor of altered mitochondrial function comprises the amount of mitochondrial DNA per mitochondrion in the sample. Thus, quantification of mitochondrial DNA may not be an indicator of altered mitochondrial function according to the present invention, but quantification of mitochondrial DNA may be a co-predictor of altered mitochondrial function or a co-indicator of altered mitochondrial function, as provided herein.

Quantification of mitochondrial DNA (mtDNA) content may be accomplished by any of a variety of established techniques that are useful for this purpose, including but not limited to oligonucleotide probe hybridization or polymerase chain reaction (PCR) using oligonucleotide primers specific for mitochondrial DNA sequences (see, e.g., Miller et al. 1996 *J. Neurochem.* 67:1897; Fahy et al., 1997 *Nucl. Ac. Res.* 25:3102; U.S. patent application Ser. No. 09/098, 079; Lee et al., 1998 *Diabetes Res. Clin. Practice* 42:161, Lee et al., 1997 *Diabetes* 46(suppl. 1):175A). A particularly useful method is the primer extension assay disclosed by Fahy et al. (*Nucl. Acids Res.* 25:3102, 1997) and by Ghosh et al. (*Am. J. Hum. Genet.* 58:325, 1996). Suitable hybridization conditions may be found in the cited references or may be varied according to the particular nucleic acid target and oligonucleotide probe selected, using methodologies well known to those having ordinary skill in the art (see, e.g., Ausubel et al., *Current Protocols in Molecular Biology*, Greene Publishing, 1987; Sambrook et al., *Molecular Cloning: A Laboratory Manual*, Cold Spring Harbor Press, 1989).

Examples of other useful techniques for determining the amount of specific nucleic acid target sequences (e.g., mtDNA) present in a sample based on specific hybridization of a primer to the target sequence include specific amplification of target nucleic acid sequences and quantification of amplification products, including but not limited to polymerase chain reaction (PCR, Gibbs et al., *Nucl. Ac. Res.* 17:2437, 1989), transcriptional amplification systems (e.g., Kwoh et al., 1989 *Proc. Nat. Acad. Sci.* 86:1173); strand displacement amplification (e.g., Walker et al., *Nucl. Ac. Res.* 20:1691, 1992; Walker et al., *Proc. Nat. Acad. Sci.* 89:392, 1992) and self-sustained sequence replication (3SR, see, e.g., Ghosh et al. in Molecular Methods for Virus Detection, 1995 Academic Press, NY, pp. 287–314; Guatelli et al., *Proc. Nat. Acad. Sci.* 87:1874, 1990), the cited references for which are incorporated herein by reference in their entireties. Other useful amplification techniques include, for example, ligase chain reaction (e.g., Barany, *Proc. Nat. Acad. Sci.* 88:189, 1991), Q-beta replicase assay (Cahill et al., *Clin. Chem.* 37:1482, 1991; Lizardi et al., *Biotechnol.* 6:1197, 1988; Fox et al., *J. Clin. Lab. Analysis* 3:378, 1989) and cycled probe technology (e.g., Cloney et al., *Clin. Chem.* 40:656, 1994), as well as other suitable methods that will be known to those familiar with the art.

Sequence length or molecular mass of primer extension assay products may be determined using any known method for characterizing the size of nucleic acid sequences with which those skilled in the art are familiar. In a preferred embodiment, primer extension products are characterized by gel electrophoresis. In another embodiment, primer extension products are characterized by mass spectrometry (MS), which may further include matrix assisted laser desorption ionization/time of flight (MALDI-TOF) analysis or other MS techniques known to those skilled in the art. See, for example, U.S. Pat. Nos. 5,622,824, 5,605,798 and 5,547,835. In another embodiment, primer extension products are characterized by liquid or gas chromatography, which may further include high performance liquid chromatography (HPLC), as chromatography-mass spectrometry (GC-MS) or other well known chromatographic methodologies.

INDICATORS OF ALTERED MITOCHONDRIAL FUNCTION THAT ARE CELLULAR RESPONSES TO ELEVATED INTRACELLULAR CALCIUM

Certain aspects of the present invention, as it relates to the correlation of type 2 DM with an indicator of altered mitochondrial function, involve monitoring intracellular calcium homeostasis and/or cellular responses to perturbations of this homeostasis, including physiological and pathophysiological calcium regulation. In particular, according to these aspects, the method of the present invention is directed to identifying a risk for type 2 DM in a subject by comparing a cellular response to elevated intracellular calcium in a biological sample from the subject with that of a control subject. The range of cellular responses to elevated intracellular calcium is broad, as is the range of methods and reagents for the detection of such responses. Many specific cellular responses are known to those having ordinary skill in the art; these responses will depend on the particular cell types present in a selected biological sample. It is within the contemplation of the present invention to provide a method for identifying a risk for type 2 DM by comparing a cellular response to elevated intracellular calcium, where such response is an indicator of altered mitochondrial function as provided herein. As non-limiting examples, cellular responses to elevated intracellular calcium include secretion of specific secretory products, exocytosis of particular preformed components, increased glycogen metabolism and cell proliferation (see, e.g., Clapham, 1995 *Cell* 80:259; Cooper, *The Cell—A Molecular Approach*, 1997 ASM Press, Washington, D.C.; Alberts, B., Bray, D., et al., *Molecular Biology of the Cell*, 1995 Garland Publishing, NY).

As a brief background, normal alterations of intramitochondrial $Ca^{2+}$ are associated with normal metabolic regulation (Dykens, 1998 in *Mitochondria & Free Radicals in Neurodegenerative Diseases*, Beal, Howell and Bodis-Wollner, Eds., Wiley-Liss, New York, pp. 29–55; Radi et al., 1998 in *Mitochondria & Free Radicals in Neurodegenerative Diseases*, Beal, Howell and Bodis-Wollner, Eds., Wiley-Liss, New York, pp. 57–89; Gunter and Pfeiffer, 1991, *Am. J. Physiol.* 27: C755; Gunter et al., 1994, Am. J. Physiol. 267: 313). For example, fluctuating levels of mitochondrial free $Ca^{2+}$ may be responsible for regulating oxidative metabolism in response to increased ATP utilization, via allosteric regulation of enzymes (reviewed by Crompton et al., 1993 *Basic Res. Cardiol.* 88: 513–523;) and the glycerophosphate shuttle (Gunter et al., 1994 *J. Bioenerg. Biomembr.* 26: 471).

Normal mitochondrial function includes regulation of cytosolic free calcium levels by sequestration of excess $Ca^{2+}$ within the mitochondrial matrix. Depending on cell type, cytosolic $Ca^{2+}$ concentration is typically 50–100 nM. In normally functioning cells, when $Ca^{2+}$ levels reach 200–300 mM, mitochondria begin to accumulate $Ca^{2+}$ as a function of the equilibrium between influx via a $Ca^{2+}$ uniporter in the inner mitochondrial membrane and $Ca^{2+}$ efflux via both $Na^+$ dependent and $Na^+$ independent calcium carriers. In certain instances, such perturbation of intracellular calcium homeostasis is a feature of diseases (such as type 2 DM) associated with altered mitochondrial function, regardless of whether the calcium regulatory dysfunction is causative of, or a consequence of, altered mitochondrial function.

Elevated mitochondrial calcium levels thus may accumulate in response to an initial elevation in cytosolic free calcium, as described above. Such elevated mitochondrial calcium concentrations in combination with reduced ATP or other conditions associated with mitochondrial pathology, can lead to collapse of mitochondrial inner membrane potential (see Gunter et al., 1998 *Biochim. Biophys. Acta* 1366:5; Rottenberg and Marbach, 1990, *Biochim. Biophys. Acta* 1016:87). Generally, in order to practice the subject invention method for identifying a risk for type 2 DM in an individual, the extramitochondrial (cytosolic) level of $Ca^{2+}$ in a biological sample is greater than that present within mitochondria. In the case of type 2 DM, mitochondrial or cytosolic calcium levels may vary from the above ranges and may range from, e.g., about 1 nM to about 500 mM, more typically from about 10 nM to about 100 $\mu$M and usually from about 20 nM to about 1 $\mu$M, where "about" indicates ±10%. A variety of calcium indicators are known in the art, including but not limited to, for example, fura-2 (McCormack et al., 1989 *Biochim. Biophys. Acta* 973:420); mag-fura-2; BTC (U.S. Pat. No. 5,501,980); fluo-3, fluo-4 and fluo-5N (U.S. Pat. No. 5,049,673); rhod-2; benzothiaza-1; and benzothiaza-2 (all of which are available from Molecular Probes, Eugene, Oreg.). These or any other means for monitoring intracellular calcium are contemplated according to the subject invention method for identifying a risk for type 2 DM.

For monitoring an indicator of altered mitochondrial function that is a cellular response to elevated intracellular calcium, compounds that induce increased cytoplasmic and mitochondrial concentrations of $Ca^{2+}$, including calcium ionophores, are well known to those of ordinary skill in the art, as are methods for measuring intracellular calcium and intramitochondrial calcium (see, e.g., Gunter and Gunter, 1994 *J. Bioenerg. Biomembr.* 26: 471; Gunter et al., 1998

*Biochim. Biophys. Acta* 1366:5; McCormack et al., 1989 *Biochim. Biophys. Acta* 973:420; Orrenius and Nicotera, 1994 *J. Neural. Transm. Suppl.* 43:1; Leist and Nicotera, 1998 *Rev. Physiol. Biochem. Pharmacol.* 132:79; and Haugland, 1996 *Handbook of Fluorescent Probes and Research Chemicals—Sixth Ed.*, Molecular Probes, Eugene, Oreg.). Accordingly, a person skilled in the art may readily select a suitable ionophore (or another compound that results in increased cytoplasmic and/or mitochondrial concentrations of $Ca^{2+}$) and an appropriate means for detecting intracellular and/or intramitochondrial calcium for use in the present invention, according to the instant disclosure and to well known methods.

$Ca^{2+}$ influx into mitochondria appears to be largely dependent, and may be completely dependent, upon the negative transmembrane electrochemical potential ($\Delta\psi$) established at the inner mitochondrial membrane by electron transfer, and such influx fails to occur in the absence of $\Delta\psi$ even when an eight-fold $Ca^{2+}$ concentration gradient is imposed (Kapus et al., 1991 *FEBS Lett.* 282:61). Accordingly, mitochondria may release $Ca^{2+}$ when the membrane potential is dissipated, as occurs with uncouplers like 2,4-dinitrophenol and carbonyl cyanide p-trifluoromethoxyphenylhydrazone (FCCP). Thus, according to certain embodiments of the present invention, collapse of $\Delta\psi$ may be potentiated by influxes of cytosolic free calcium into the mitochondria, as may occur under certain physiological conditions including those encountered by cells of a subject having type 2 DM. Detection of such collapse may be accomplished by a variety of means as provided herein.

Typically, mitochondrial membrane potential may be determined according to methods with which those skilled in the art will be readily familiar, including but not limited to detection and/or measurement of detectable compounds such as fluorescent indicators, optical probes and/or sensitive pH and ion-selective electrodes (See. e.g., Ernster et al., 1981 *J. Cell Biol.* 91:227s and references cited; see also Haugland, 1996 *Handbook of Fluorescent Probes and Research Chemicals—Sixth Ed.*, Molecular Probes, Eugene, Oreg., pp. 266–274 and 589–594.). For example, by way of illustration and not limitation, the fluorescent probes 2-,4-dimethylaminostyryl-N-methyl pyridinium (DASPMI) and tetramethylrhodamine esters (such as, e.g., tetramethylrhodamine methyl ester, TMRM; tetramethylrhodamine ethyl ester, TMRE) or related compounds (see, e.g., Haugland, 1996, supra) may be quantified following accumulation in mitochondria, a process that is dependent on, and proportional to, mitochondrial membrane potential (see, e.g. Murphy et al., 1998 in *Mitochondria & Free Radicals in Neurodegenerative Diseases*, Beal, Howell and Bodis-Wollner, Eds., Wiley-Liss, New York, pp. 159–186 and references cited therein; and *Molecular Probes On-line Handbook of Fluorescent Probes and Research Chemicals*, at http://www.probes.com/handbook/toc.html). Other fluorescent detectable compounds that may be used in the invention include but are not limited to rhodamine 123, rhodamine B hexyl ester, $DiOC_6(3)$, JC-1 [5,5',6,6'-Tetrachloro- 1,1',3,3'-Tetraethylbezimidazolcarbocyanine Iodide] (see Cossarizza, et al., 1993 *Biochem. Biophys. Res. Comm.* 197:40; Reers et al., 1995 *Meth. Enzymol.* 260:406), rhod-2 (see U.S. Pat. No. 5,049,673; all of the preceding compounds are available from Molecular Probes, Eugene, Oreg.) and rhodamine 800 (Lambda Physik, GmbH, Göttingen, Germany; see Sakanoue et al., 1997 *J. Biochem.* 121:29). Methods for monitoring mitochondrial membrane potential are also disclosed in U.S. application Ser. No. 09/161,172.

Mitochondrial membrane potential can also be measured by non-fluorescent means, for example by using TTP (tetraphenylphosphonium ion) and a TTP-sensitive electrode (Kamo et al., 1979 *J. Membrane Biol.* 49:105; Porter and Brand, 1995 *Am. J. Physiol.* 269:R1213). Those skilled in the art will be able to select appropriate detectable compounds or other appropriate means for measuring $\Delta\psi m$. By way of example and not limitation, TMRM is somewhat preferable to TMRE because, following efflux from mitochondria, TMRE yields slightly more residual signal in the endcplasmic reticulicum and cytoplasm than TMRM.

As another non-limiting example, membrane potential may be additionally or alternatively calculated from indirect measurements of mitochondrial permeability to detectable charged solutes, using matrix volume and/or pyridine nucleotide redox determination combined with spectrophotometric or fluorimetric quantification. Measurement of membrane potential dependent substrate exchange-diffusion across the inner mitochondrial membrane may also provide an indirect measurement of membrane potential. (See, e.g., Quinn. 1976, *The Molecular Biology of Cell Membranes*, University Park Press, Baltimore, Md., pp. 200–217 and references cited therein.)

Exquisite sensitivity to extraordinary mitochondrial accumulations of $Ca^{2+}$ that result from elevation of intracellular calcium, as described above, may also characterize type 2 DM. Such mitochondrial sensitivity may provide an indicator of altered mitochondrial function according to the present invention. Additionally, a variety of physiologically pertinent agents, including hydroperoxide and free radicals, may synergize with $Ca^{2+}$ to induce collapse of $\Delta\psi$ (Novgorodov et al., 1991 *Biochem. Biophys. Acta* 1058: 242; Takeyama et al., 1993 *Biochem. J.* 294: 719; Guidox et al., 1993 *Arch. Biochem. Biophys.* 306:139).

INDICATORS OF ALTERED MITOCHONDRIAL FUNCTION THAT ARE CELLULAR RESPONSES TO APOPTOGENIC STIMULI

Turning to another aspect, the present invention relates to the correlation of type 2 DM with an indicator of altered mitochondrial function, involving programmed cell death or apoptosis. In particular, according to this aspect, the present invention is directed to a method comprising comparing a cellular response to an apoptosis-inducing ("apoptogenic") stimulus in a biological sample from (i) a subject believed to be at risk for type 2 DM, and (ii) a control subject. The range of cellular responses to various known apoptogenic stimuli is broad, as is the range of methods and reagents for the detection of such responses. It is within the contemplation of the present invention to provide a method for identifying a risk for type 2 DM by comparing a cellular response to an apoptogenic stimulus, where such response is an indicator of altered mitochondrial function as provided herein.

By way of background, mitochondrial dysfunction is thought to be critical in the cascade of events leading to apoptosis in various cell types (Kroemer et al., *FASEB J.* 9:1277–87, 1995). Altered mitochondrial physiology may be among the earliest events in programmed cell death (Zamzami et al., *J. Exp. Med.* 182:367–77, 1995; Zamzami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994). In several cell types, reduction in the mitochondrial membrane potential ($\Delta\psi m$) precedes the nuclear DNA degradation that accompanies apoptosis. In cell-free systems, mitochondrial, but not nuclear, enriched fractions are capable of inducing nuclear apoptosis (Newmeyer et al., Cell 70:353–64, 1994). Perturbation of mitochondrial respiratory activity leading to altered cellular metabolic states, such as elevated intracellular ROS, may occur in type 2 DM and may further induce pathogenetic events via apoptotic mechanisms.

Oxidatively stressed mitochondria may release a preformed soluble factor that can induce chromosomal condensation, an event preceding apoptosis (Marchetti et al. Cancer Res. 56:2033–38, 1996). In addition, members of the Bcl-2 family of anti-apoptosis gene products are located within the outer mitochondrial membrane (Monaghan et al., J. Histochem. Cytochem. 40:1819–25, 1992) and these proteins appear to protect membranes from oxidative stress (Korsmeyer et al, Biochim. Biophys. Act. 1271:63, 1995). Localization of Bcl-2 to this membrane appears to be indispensable for modulation of apoptosis (Nguyen et al., J. Biol. Chem. 269:16521–24, 1994). Thus, changes in mitochondrial physiology may be important mediators of apoptosis.

Altered mitochondrial function, as may be used to identify a risk for type 2 DM in a subject according to the present disclosure, may therefore lower the threshold for induction of apoptosis by an apoptogen. A variety of apoptogens are known to those familiar with the art (see, e.g., Green et al., 1998 Science 281:1309 and references cited therein) and may include by way of illustration and not limitation: tumor necrosis factor-alpha (TNF-α); Fas ligand; glutamate; N-methyl-D-aspartate (NMDA); interleukin-3 (IL-3); herbimycin A (Mancini et al., 1997 J. Cell. Biol. 138:449–469); paraquat (Costantini et al., 1995 Toxicology 99:1–2); ethylene glycols; protein kinase inhibitors, such as. e.g. staurosporine, calphostin C, caffeic acid phenethyl ester, chelerythrine chloride, genistein; 1-(5-isoquinolinesulfonyl)-2-methylpiperazine N-[2-((p-bromocinnamyl)amino)ethyl]-5-5-isoquinolinesulfonamide, KN-93; quercitin; d-erythro-sphingosine derivatives; UV irradiation; ionophores such as, e.g: ionomycin and valinomycin; MAP kinase inducers such as, e.g.: anisomycin, anandamine; cell cycle blockers such as. e.g.: aphidicolin, colcemid, 5-fluorouracil, homoharringtonine; acetylcholinesterase inhibitors such as, e.g. berberine; anti-estrogens such as, e.g.: tamoxifen; pro-oxidants, such as. e.g.: tert-butyl peroxide, hydrogen peroxide; free radicals such as, e.g., nitric oxide; inoroanic metal ions, such as, e.g., cadmium; DNA synthesis inhibitors such as, e.g.: actinomycin D; DNA intercalators such as, e.g., doxorubicin, bleomycin sulfate, hydroxyurea, methotrexate, mitomycin C, camptothecin, daunorubicin; protein synthesis inhibitors such as, e.g., cycloheximide, puromycin, rapamycin; agents that affect microtubulin formation or stability such as, e.g.: vinblastine, vincristine, colchicine, 4-hydroxyphenylretinamide, paclitaxel; Bad protein, Bid protein and Bax protein (see, e.g. Jurgenmeier et al. 1998 Proc. Nat. Acad Sci. USA 95:4997–5002 and references cited therein); calcium and inorganic phosphate (Kroemer et al., 1998 Ann. Rev. Physiol. 60:619).

In one embodiment of the subject invention method wherein the indicator of altered mitochondrial function is a cellular response to an apoptogen, cells in a biological sample that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by a person having ordinary skill in the art, for example by using light microscopy. As another example, cells undergoing apoptosis may exhibit fragmentation and disintegration of chromosomes, which may be apparent by microscopy and/or through the use of DNA-specific or chromatin-specific dyes that are known in the art, including fluorescent dyes. Such cells may also exhibit altered plasma membrane permeability properties as may be readily detected through the use of vital dyes (e.g. propidium iodide, trypan blue) or by the detection of lactate dehydrogenase leakage into the extracellular milieu. These and other means for detecting apoptotic cells by morphologic criteria, altered plasma membrane permeability and related changes will be apparent to those familiar with the art.

In another embodiment of the subject invention method wherein the indicator of altered mitochondrial function is a cellular response to an apoptogen, cells in a biological sample may be assayed for translocation of cell membrane phosphatidylserine (PS) from the inner to the outer leaflet of the plasma membrane, which may be detected, for example, by measuring outer leaflet binding by the PS-specific protein annexin. (Martin et al., J. Exp. Med. 182:1545, 1995; Fadok et al., J. Immunol. 148:2207, 1992.) In still another embodiment of this aspect of the invention, a cellular response to an apoptogen is determined by an assay for induction of specific protease activity in any member of a family of apoptosis-activated proteases known as the caspases (see, e.g., Green et al., 1998 Science 281:1309). Those having ordinary skill in the art will be readily familiar with methods for determining caspase activity, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., 1997 J. Neurosci. 17:6165). The synthetic peptide Z-Tyr-Val-Ala-Asp-AFC (SEQ ID NO:__;), wherein "Z" indicates a benzoyl carbonyl moiety and AFC indicates 7-amino-4-trifluoromethylcoumarin (Kluck et al., 1997 Science 275:1132; Nicholson et al., 1995 Nature 376:37), is one such substrate. Other non-limiting examples of substrates include nuclear proteins such as U1-70 kDa and DNA-PKcs (Rosen and Casciola-Rosen, 1997 J. Cell. Biochem. 64:50; Cohen, 1997 Biochem. J. 326:1).

As described above, the mitochondrial inner membrane may exhibit highly selective and regulated permeability for many small solutes, but is impermeable to large (>~10 kDa) molecules. (See, e.g., Quinn, 1976 The Molecular Biology of Cell Membranes. University Park Press, Baltimore, Md.). In cells undergoing apoptosis, however, collapse of mitochondrial membrane potential may be accompanied by increased permeability permitting macromolecule diffusion across the mitochondrial membrane. Thus, in another embodiment of the subject invention method wherein the indicator of altered mitochondrial function is a cellular response to an apoptogen, detection of a mitochondrial protein, for example cytochrome c that has escaped from mitochondria in apoptotic cells, may provide evidence of a response to an apoptogen that can be readily determined. (Liu et al. Cell 86:147, 1996) Such detection of cytochrome c may be performed spectrophotometrically, immunochemically or by other well established methods for determining the presence of a specific protein.

For instance, release of cytochrome c from cells challenged with apoptotic stimuli (e.g., ionomycin, a well known calcium ionophore) can be followed by a variety of immunological methods. Matrix-assisted laser desorption ionization time-of-flight (MALDI-TOF) mass spectrometry coupled with affinity capture is particularly suitable for such analysis since apo-cytochrome c and holo-cytochrome c can be distinguished on the basis of their unique molecular weights. For example, the Surface-Enhanced Laser Desorption/Ionization (SELDI™) system (Ciphergen, Palo Alto, Calif.) may be utilized to detect cytochrome c release from mitochondria in apoptogen treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular mass of the protein is determined by its time of flight to the detector of the SELDI™ mass spectrometer.

A person having ordinary skill in the art will readily appreciate that there may be other suitable techniques for quantifying apoptosis, and such techniques for purposes of determining an indicator of altered mitochondrial function that is a cellular response to an apoptogenic stimulus are within the scope of the methods provided by the present invention.

FREE RADICAL PRODUCTION AS AN INDICATOR OF ALTERED MITOCHONDRIAL FUNCTION

In certain embodiments of the present invention, free radical production in a biological sample may be detected as an indicator of altered mitochondrial function. Although mitochondria are a primary source of free radicals in biological systems (see, e.g., Murphy et al., 1998 in *Mitochondria and Free Radicals in Neurodegenerative Diseases*, Beal, Howell and Bodis-Wollner, Eds., Wiley-Liss, New York, pp. 159–186 and references cited therein), the invention should not be so limited and free radical production can be an indicator of altered mitochondrial function regardless of the particular subcellular source site. For example, numerous intracellular biochemical pathways that lead to the formation of radicals through production of metabolites such as hydrogen peroxide, nitric oxide or superoxide radical via reactions catalyzed by enzymes such as flavin-linked oxidases, superoxide dismutase or nitric oxide synthetase, are known in the art, as are methods for detecting such radicals (see, e.g., Kelver, 1993 *Crit. Rev. Toxicol.* 23:21; Halliwell B. and J. M. C. Gutteridge, *Free Radicals in Biology and medicine*, 1989 Clarendon Press, Oxford, UK; Davies, K. J. A. and F. Ursini, *The Oxygen Paradox*. Cleup Univ. Press, Padova, IT). Altered mitochondrial function, such as failure at any step of the ETC, may also lead to the generation of highly reactive free radicals. As noted above, radicals resulting from altered mitochondrial function include reactive oxygen species (ROS), for example, superoxide, peroxynitrite and hydroxyl radicals, and potentially other reactive species that may be toxic to cells. Accordingly, in certain preferred embodiments of the invention an indicator of altered mitochondrial function may be a detectable free radical species present in a biological sample. In certain particularly preferred embodiments, the detectable free radical will be a ROS.

Methods for detecting a free radical that may be useful as an indicator of altered mitochondrial function are known in the art and will depend on the particular radical. Typically, a level of free radical production in a biological sample may be determined according to methods with which those skilled in the art will be readily familiar, including but not limited to detection and/or measurement of: glycoxidation products including pentosidine, carboxymethylysine and pyrroline; lipoxidation products including glyoxal, malondialdehyde and 4-hydroxynonenal; thiobarbituric acid reactive substances (TBARS; see, e.g., Steinbrecher et al., 1984 *Proc. Nat. Acad. Sci. USA* 81:3883; Wolff, 1993 *Br. Med. Bull.* 49:642) and/or other chemical detection means such as salicylate trapping of hydroxyl radicals (e.g. Ghiselli et al., 1998 *Meths. Mol. Biol.* 108:89; Halliwell et al., 1997 *Free Radic. Res.* 27:239) or specific adduct formation (see, e.g., Mecocci et al. 1993 *Ann. Neurol.* 34:609; Giulivi et al., 1994 *Meths. Enzymol.* 233:363) including malondialdehyde formation, protein nitrosylation, DNA oxidation including mitochondrial DNA oxidation, 8'-OH-guanosine adducts (e.g., Beckman et al., 1999 *Mutat. Res.* 424:51), protein oxidation, protein carbonyl modification (e.g., Baynes et al., 1991 *Diabetes* 40:405: Baynes et al., 1999 *Diabetes* 48:1); electron spin resonance (ESR) probes; cyclic voltametry; fluorescent andlor chemiluminescent indicators (see also e.g., Greenwald, R. A. (ed.), *Handbook of Methods for Oxygen Radical Research*, 1985 CRC Press, Boca Raton, Fla. Acworth and Bailey, (eds.), *Handbook of Oxidative Metabolism*, 1995 ESA, Inc. Chelmsford, Mass.; Yla-Herttuala et al., 1989 *J. Clin. Invest.* 84:1086: Velazques et al., 1991 *Diabetic Medicine* 8:752; Belch et al., 1995 *Int. Angiol.* 14:385; Sato et al., 1979 *Biochem. Med.* 21:104; Traverso et al., 1998 *Diabetologia* 41:265; Haugland, 1996 *Handbook of Fluorescent Probes and Research Chemicals—Sixth Ed.*, Molecular Probes, Eugene, Oreg., pp. 483–502, and references cited therein). For example, by way of illustration and not limitation, oxidation of the fluorescent probes dichlorodihydrofluorescein diacetate and its carboxylated derivative carboxydichlorodihydrofluorescein diacetate (see, e.g., Haugland, 1996, supra) may be quantified following accumulation in cells, a process that is dependent on, and proportional to, the presence of reactive oxygen species (see also, e.g., *Molecular Probes On-line Handbook of Fluorescent Probes and Research Chemicals*, at http://www.probes.com/handbook/toc.html). Other fluorescent detectable compounds that may be used in the invention for detection of free radical production include but are not limited to dihydrorhodamine and dihydrorosamine derivatives, cis-parinaric acid, resorufin derivatives, lucigenin and any other suitable compound that may be known to those familiar with the art.

Thus, as also described above, free radical mediated damage may inactivate one or more of the myriad proteins of the ETC and in doing so, may uncouple the mitochondrial chemiosmotic mechanism responsible for oxidative phosphorylation and ATP production. Indicators of altered mitochondrial function that are ATP biosynthesis factors, including determination of ATP production, are described in greater detail herein. Free radical mediated damage to mitochondrial functional integrity is also just one example of multiple mechanisms associated with altered mitochondrial function that may result in collapse of the electrochemical potential maintained by the inner mitochondrial membrane. Methods for detecting changes in the inner mitochondrial membrane potential are described above and in co-pending U.S. patent application Ser. No. 09/161,172.

SAMPLES

Biological samples may comprise any tissue or cell preparation in which at least one candidate indicator of altered mitochondrial function can be detected, and may vary in nature accordingly, depending on the particular indicator(s) to be compared. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like. In certain preferred embodiments of the invention, the subject or biological source may be suspected of having or being at risk for having type 2 diabetes mellitus, and in certain preferred embodiments of the invention the subject or biological source may be known to be free of a risk or presence of such as disease.

In certain other preferred embodiments where it is desirable to determine whether or not a subject or biological source falls within clinical parameters indicative of type 2 diabetes mellitus, signs and symptoms of type 2 diabetes that are accepted by those skilled in the art may be used to so designate a subject or biological source, for example clinical signs referred to in Gavin et al. (*Diabetes Care* 22(suppl. 1):S5–S19, 1999, American Diabetes Association Expert Committee on the Diagnosis and Classification of Diabetes Mellitus) and references cited therein, or other means known in the art for diagnosing type 2 diabetes.

In certain aspects of the invention, biological samples containing at least one candidate indicator (or co-indicator as provided herein) of altered mitochondrial function may be obtained from the subject or biological source before and after contacting the subject or biological source with a candidate agent, for example to identify a candidate agent capable of effecting a change in the level of the indicator (or co-indicator) of altered mitochondrial function as defined above, relative to the level before exposure of the subject or biological source to the agent. The indicator (or co-indicator) may optionally, in certain preferred embodiments wherein the indicator (or co-indicator) is an enzyme or an ATP biosynthesis factor, be determined as a measure of enzyme (or ATP biosynthesis factor) catalytic activity in the sample, as a measure of enzyme (or ATP biosynthesis factor) quantity in the sample or as a measure of enzyme (or ATP biosynthesis factor) expression level in the sample, as provided herein.

In a most preferred embodiment of the invention, the biological sample containing at least one candidate indicator (or co-indicator) of altered mitochondrial function comprises a skeletal muscle biopsy. In another preferred embodiment of the invention, the biological sample containing at least one candidate indicator (or co-indicator) of altered mitochondrial function may comprise whole blood, and may in another preferred embodiment comprise a crude buffy coat fraction of whole blood, which is known in the art to comprise further a particulate fraction of whole blood enriched in white blood cells and platelets and substantially depleted of erythrocytes. Those familiar with the art will know how to prepare such a buffy coat fraction, which may be prepared by differential density sedimentation of blood components under defined conditions, including the use of density dependent separation media, or by other methods. In other preferred embodiments, the biological sample containing at least one indicator (or co-indicator) of altered mitochondrial function may comprise an enriched, isolated or purified blood cell subpopulation fraction such as, for example, lymphocytes, polymorphonuclear leukocytes, granulocytes and the like. Methods for the selective preparation of particular hematopoietic cell subpopulations are well known in the art (see, e.g., *Current Protocols in Immunology*, J. E. Coligan et al., (Eds.) 1998 John Wiley & Sons, NY).

According to certain embodiments of the invention, the particular cell type or tissue type from which a biological sample is obtained may influence qualitative or quantitative aspects of at least one candidate indicator (or co-indicator) of altered mitochondrial function contained therein, relative to the corresponding candidate indicator (or co-indicator) of altered mitochondrial function obtained from distinct cell or tissue types of a common biological source. It is therefore within the contemplation of the invention to quantify at least one candidate indicator (or co-indicator) of altered mitochondrial function in biological samples from different cell or tissue types as may render the advantages of the invention most useful for type 2 diabetes mellitus, and further for a particular degree of progression of known or suspected type 2 diabetes. The relevant cell or tissue types will be known to those familiar with such diseases.

For example, as provided herein, skeletal muscle may represent a particularly preferred tissue type in which oxidative energy demand (e.g., ATP demand) is high and is requried for normal glucose utilization. Accordingly, other biological samples derived from cell or tissue types that use mitochondrial ATP for cellular functions involved in glucose homeostasis, for example pancreatic beta cells and adipose cells, may also be particularly useful.

In order to determine whether a mitochondrial alteration may contribute to a particular disease state, it may be useful to construct a model system for diagnostic tests and for screening candidate therapeutic agents in which the nuclear genetic background may be held constant while the mitochondrial genome is modified. It is known in the art to deplete mitochondrial DNA from cultured cells to produce $\rho^0$ cells, thereby preventing expression and replication of mitochondrial genes and inactivating mitochondrial function. It is further known in the art to repopulate such $\rho^0$ cells with mitochondria derived from foreign cells in order to assess the contribution of the donor mitochondrial genotype to the respiratory phenotype of the recipient cells. Such cytoplasmic hybrid cells, containing genomic and mitochondrial DNAs of differing biological origins, are known as cybrids. See, for example, International Publication Number WO 95/26973 and U.S. Pat. No. 5,888,498 which are hereby incorporated by reference in their entireties, and references cited therein.

According to the present invention, a level of at least one indicator (or co-indicator) of altered mitochondrial function is determined in a biological sample from a subject or biological source. For subjects that are asymptomatic, that exhibit IGT or that meet clinical criteria for having or being at risk for having type 2 DM (Gavin et al. *Diabetes Care* 22(suppl. 1):S5–S19, 1999, American Diabetes Association Expert Committee on the Diagnosis and Classification of Diabetes Mellitus), such determination may have prognostic and/or diagnostic usefulness. For example, where other clinical indicators of type 2 DM are known, levels of at least one indicator of altered mitochondrial function in subjects known to be free of a risk or presence of type 2 DM based on the absence of these indicators may be determined to establish a control range for such level(s). The levels may also be determined in biological samples obtained from subjects suspected of having or being at risk for having type 2 DM, and compared to the control range determined in disease free subjects. Those having familiarity with the art will appreciate that there may be any number of variations on the particular subjects, biological sources and bases for comparing levels of at least one indicator of altered mitochondrial function that are useful beyond those that are expressly presented herein, and these additional uses are within the scope and spirit of the invention.

For instance, determination of levels of at least one indicator (or co-indicator) of altered mitochondrial function may take the form of a prognostic or a diagnostic assay performed on a skeletal muscle biopsy, on whole blood collected from a subject by routine venous blood draw, on buffy coat cells prepared from blood or on biological samples that are other cells, organs or tissue from a subject. Alternatively, in certain situations it may be desirable to construct cybrid cell lines using mitochondria from either control subjects or subjects suspected of being at risk for type 2 DM. Such cybrids may be used to determine levels of at least one indicator of altered mitochondrial function for diagnostic or predictive purposes, or as biological sources for screening assays to identify agents that may be suitable for treating type 2 DM based on their ability to alter the levels of at least one indicator of altered mitochondrial function in treated cells.

In one embodiment of this aspect of the invention, therapeutic agents or combinations of agents that are tailored to effectively treat an individual patient's particular disease may be identified by routine screening of candidate agents on cybrid cells constructed with the patient's mitochondria. In another embodiment, a method for identifying subtypes of type 2 DM is provided, for example, based on differential effects of individual candidate agents on cybrid cells constructed using mitochondria from different type 2 DM subjects.

In other embodiments, the invention provides a method of identifying an agent suitable for treating a subject suspected of being at risk for having type 2 DM by comparing the level of at least one indicator of altered mitochondrial function, or by comparing the level of a co-indicator of altered mitochondrial function and at least one non-enzyme indicator of altered mitochondrial function, in the presence and absence of a candidate agent, to determine the suitability of the agent for treating type 2 DM. In particularly preferred embodiments, the agent is a small molecule.

Candidate agents for use in a method of screening for a modulator of an indicator of altered mitochondrial function according to the present invention may be provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. For example, members of a library of test compounds can be administered to a plurality of samples, and then assayed for their ability to increase or decrease the level of at least one indicator of altered mitochondrial function.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g. PCT/US91/08694, PCT/US91/04666, which are hereby incorporated by reference in their entireties) or other compositions that may include small molecules as provided herein (see e.g. PCT/US94/08542, EP 0774464, U.S. Pat. No. 5,798,035, U.S. Pat. No. 5,789,172, U.S. Pat. No. 5,751,629, which are hereby incorporated by reference in their entireties). Those having ordinary skill in the art will appreciate that a diverse assortment of such libraries may be prepared according to established procedures, and tested for their influence on an indicator of altered mitochondrial function, according to the present disclosure.

The present invention provides compositions and methods that are useful in pharmacogenomics, for the classification and/or stratification of a subject or patient population. In one embodiment, for example, such stratification may be achieved by identification in a subject or patient population of one or more distinct profiles of at least one indicator (or co-indicator) of altered mitochondrial function that correlate with type 2 DM. Such profiles may define parameters indicative of a subject's predisposition to develop type 2 DM, and may further be useful in the identification of novel subtypes of type 2 DM. In another embodiment, correlation of one or more traits in a subject with at least one indicator (or co-indicator) of altered mitochondrial function may be used to gauge the subject's responsiveness to, or the efficacy of, a particular therapeutic treatment. In another embodiment of the invention, measurement of the level(s) of at least one indicator (or co-indicator) of altered mitochondrial function in a biological sample from a subject is combined with identification of the subject's potential IGT status to determine the risk for, or presence of type 2 DM in the subject. By using the combination of the methods for determining levels of at least one indicator of altered mitochondrial function as disclosed herein, and methods known in the art for determining the presence of IGT or type 2 DM (Gavin et al. *Diabetes Care* 22(suppl. 1):S5–S19, 1999), an enhanced ability to detect the relative risk for type 2 DM is provided by the instant invention along with other related advantages. Similarly, where levels of at least one indicator (or co-indicator) of altered mitochondrial function and risk for type 2 DM are correlated, the present invention provides advantageous methods for identifying agents suitable for treating type 2 DM, where such agents affect levels of at least one indicator of altered mitochondrial function in a biological source.

As described herein, determination of levels of at least one indicator of altered mitochondrial function may also be used to stratify a type 2 DM patient population (i.e., a population classified as having type 2 DM by independent criteria). Accordingly, in another preferred embodiment of the invention, determination of levels of at least one indicator of altered mitochondrial function in a biological sample from a type 2 DM subject may provide a useful correlative indicator for that subject. A type 2 DM subject so classified on the basis of levels of at least one indicator of altered mitochondrial function may be monitored using type 2 DM clinical parameters referred to above, such that correlation between levels of at least one indicator of altered mitochondrial function and any particular clinical score used to evaluate type 2 DM may be monitored. For example, stratification of a type 2 DM patient population according to levels of at least one indicator of altered mitochondrial function may provide a useful marker with which to correlate the efficacy of any candidate therapeutic agent being used in type 2 DM subjects.

In certain other embodiments, the invention provides a method of treating a patient having type 2 DM by administering to the patient an agent that substantially restores at least one indicator (or co-indicator) of altered mitochondrial function to a level found in control or normal subjects. In one embodiment the indicator of altered mitochondrial function is the amount of ATP produced. In another embodiment, the indicator of altered mitochondrial function is the amount of mtDNA present. In a most preferred embodiment, an agent that substantially restores (e.g., increases or decreases) at least one indicator of altered mitochondrial function to a normal level effects the return of the level of that indicator to a level found in control subjects. In another preferred embodiment, the agent that substantially restores such an indicator confers a clinically beneficial effect on the subject. In another embodiment, the agent that substantially restores the indicator promotes a statistically significant change in the level of at least one indicator (or co-indicator or co-predictor) of altered mitochondrial function. As noted herein, those having ordinary skill in the art can readily determine whether a change in the level of a particular indicator brings that level closer to a normal value and/or clinically benefits the subject. Thus, an agent that substantially restores at least one indicator of altered mitochondrial function to a normal level may include an agent capable of fully or partially restoring such level.

These and related advantages will be appreciated by those familiar with the art.

The following Examples are offered by way of illustration and not limitation.

EXAMPLES

Example 1

ENZYME INDICATORS OF ALTERED MITOCHONDRIAL FUNCTION IN HUMAN SKELETAL MUSCLE AND CYBRID CELL LINES

Human volunteers were recruited from the San Diego Veterans Administration Medical Center Clinical Research Center (San Diego, Calif.) and classified into three groups: type 2 diabetics (type 2 DM, Gavin et al. 1999 *Diabetes Care* 22(suppl. 1):S5–S19); lean controls (body mass index <27); and obese controls (body mass index ≧27). Diagnoses of type 2 DM were confirmed with oral glucose tolerance tests. After obtaining informed consent, blood samples and a quadriceps muscle biopsy were collected from each subject (Bergstrom, 1962 *Scand. J. Clin. Lad. Invest.* 14(Suppl 68): 1–110). Briefly, an area of the anterior thigh was anesthetized by injection of 2–3 ml of 1% lidocaine (e.g., Xylocaine, Astra USA, Inc., Westboro, Mass.). A 7 mm incision was made through the skin, and a 5 mm side cutting needle inserted to dissect the muscle. The muscle fragment was quickly expelled into phosphate buffered saline, blotted on a gauze pad, and dropped into liquid nitrogen. Muscle samples were stored frozen at −80° C. until analysis. Blood samples were used for construction of cybrid cells; muscle samples were used for biochemical analyses.

Skeletal muscle obtained from biopsies was pulverized under liquid nitrogen to a fine powder. The powder was suspended in mannitol-sucrose buffer (MSB: 0.21 M mannitol, 0.7 M sucrose. 0.05 M Tris-HCl, 10 mM EDTA). and homogenized with 15 strokes in a glass-glass homogenizer. Debris was removed by centrifugation at 5000 g for 5 min. Aliquots of the supernatant were used for citrate synthase assays and western blots of "total lysate" protein. The remaining supernatants were centrifuged at 20,000 g for 15 min to pellet mitochondria. The mitochondrial pellet was suspended in Hank's Balanced Salt Solution (HBSS; Irine Scientific; Irvine, Calif.), incubated for 2 min, with 0.25 mg/ml digitonin, and sonicated using a cup-horn sonicator (Sonifier 450; Branson, Danbury, Conn.) at 50% duty cycle for 3 min. The resultant submitochondrial particles (SMP) were kept on ice until use.

To construct cytoplasmic hybrid or "cybrid" cell lines containing mtDNA from the human volunteers, SH-SY5Y neuroblastoma cells were depleted of mitochondrial DNA, and fused with patient platelets as described by Miller et al. (1996 *J. Neurochem* 67:1897–1907; see also U.S. Pat. No. 5,888,498). Briefly, from 6 ml of citrate-anticoagulated blood drawn from human subjects as described above, platelets were isolated by differential centrifugation. The cell pellet was resuspended in 1 ml calcium-free Minimal Essential Medium (MEM; Gibco BRL, Grand Island, N.Y.). $\rho^0$ SH-SY5Y cells were harvested from a 75 cm$^2$ flask by trypsinization, resuspended in 10 ml calcium-free MEM, and collected by centrifugation at 200 g for 5 minutes. The $\rho^0$ cell pellet was resuspended in 1 ml calcium-free MEM. The platelet suspension was added to the $\rho^0$ cell suspension, mixed gently, and the mixture was incubated 5 min at room temperature. The cells were collected by centrifugation at 400 g for 5 min. To promote fusion, 150 μl polyethylene glycol-1000 solution (50% w/v in calcium-free MEM; J. T. Baker, Phillipsburg, Pa.) was added with gentle mixing using a pipet. The mixture was incubated 1.5 min at room temperature, then diluted with 12 ml $\rho^0$ culture medium (Dulbecco's Modified Eagle Medium [Irvine Scientific, Irvine, Clif.], 10% fetal calf serum [Irvine Scientific, Irvine, Calif.], 1 mM sodium pyruvate, 50 μg/ml uridine, and 100 U/ml penicillin/streptomycin solution (Gibco BRL, Grand Island, N.Y.). The fused cells were transferred to a tissue culture flask and grown in a humidified 5% $CO_2$, 95% air environment at 37° C. The medium was changed daily. After 1 week, selection medium ($\rho^0$ medium lacking uridine and pyruvate) was substituted for the $\rho^0$ medium. The cybrid cells were allowed to grow and repopulate their mitochondrial DNA for 6–8 weeks before use. Cybrid cells were harvested by scraping in phosphate buffered saline (PBS, Irvine Scientific, Irvine, Calif.). Submitochondrial particles (SMP) were prepared from the cells as described below for individual enzyme assays.

Enzyme activities of citrate synthase and of mitochondrial electron transport chain complexes I and IV were measured as described by Miller et al. (1996) and Parker et al. (1994 *Neurology*, 44:1090–1096). Brief descriptions of the assays follow:

To determine citrate synthase activity in cultured cybrid cells produced as described above, 2×10$^5$ cells were added to a spectrophotometer cuvette for each group. For citrate synthase determination in clarified skeletal muscle homogenate prepared as described above, 20 μg of "total lysate" was added to each cuvette. Assay buffer (0.04% Triton X-100, 0.1 mM 5,5'-dithio-bis(2-nitrobenzoic acid), 100 mM Tris, pH 8.0) pre-warmed to 30° C. was added to each cuvette. Acetyl CoA (final concentration 50 μM) and oxaloacetic acid (final concentration 500 μM) were added to bring the assay volume to 1 ml. The change in absorbance at 412 nm was measured for 3 min, in a Beckman DU7400 spectrophotometer (Beckman Instruments, Palo Alto. Calif.).

Complex I (NADH:ubiguinone oxidoreductase) in Cultured Cells:

Cell suspensions (2 million cells/ml) were incubated with 0.005% digitonin in HBSS containing 5 mM EDTA (HBSS/EDTA) for 20 seconds at room temperature. Fifty volumes HBSS/EDTA were then added. The solution was centrifuged at 14,000 g for 10 min. at 4° C., and the pellet resuspended in HBSS/EDTA containing 1 μM pepstatin, 1 μM leupeptin and 100 μM phenylmethylsulfonyl fluoride (PMSF). The resultant solution was sonicated for 6 minutes on ice in a cup-horn sonicator (Sonifier 450: Branson, Danbury, Conn.) at 50% duty cycle, 50% power. An aliquot of the solution (30–100 μg protein) was added to a 1 ml cuvette. Coenzyme Q1 (0.042 mM final concentration). NADH (0.1 mM final concentration), and assay buffer (25 mM potassium phosphate, 0.25 mM EDTA, 1.5 mM potassium cyanide, pH 8.0) were added. The change in absorbance at 340 nM was measured for 2 minutes. Rotenone (2.5 μm final concentration) was added, and a second 2 minute reading was taken. Activity was calculated as the rate in the absence of rotenone minus the rate in the presence of rotenone.

Complex IV (cytochrome c oxidase) in Cultured Cells:

The SMP solution was prepared as described for Complex 1. Assay buffer 20 mM potassium phosphate, pH 7.0), SMP (1–50 μg protein), n-dodecyl-β-D-maltoside 0.1 mg/ml final), and cytochrome c (5 mM) were added to a cuvette in a total volume of 1 ml. The change in absorbance of reduced cytochrome c at 550 nm was measured for 90 seconds. The cyanide-inhibited rate was subtracted to yield activity.

Complex IV in Skeletal Muscle:

SMP were prepared as described above. This preparation was then substituted for the cultured cell preparation in the Complex IV assay described above.

Complex V (ATP synthase) activity was measured using a coupled spectrophotometric assay as follows: SMP were incubated in assay buffer containing 1 mM ATP, 1 mM phosphoenolpyruvate, 0.3 mM NADH, 3 U/ml pyruvate kinase, and 10 U/ml lactate dehydrogenase at 30° C. The change in absorbance at 340 nm was measured for 5 min in a Beckman DU 7400 spectrophotometer. The ATP synthase activity was expressed as nmoles NADH oxidized per minute per mg lysate or SMP protein.

Reactive Oxygen Species Production:

Production of reactive oxygen species by cybrid cells in culture was measured using the fluorescent dye dichlorodihydrofluorescein (Molecular Probes, Eugene, Oreg.) as described by Miller et al. (1996). Cells were plated at 75,000 cells per well in 96-well plates and allowed to grow overnight in a 5% $CO_2$, 95% air, humidified 37° C. incubator. The cells were rinsed with HBSS, then incubated with HBSS containing 30 μM 2',7'-dichlorodihydrofluorescein diacetate (Molecular Probes, Eugene, Oreg.) for 2 hr. After rinsing with HBSS, the fluorescence was measured using a Cytofluor model 2350 plate reader (Millipore, Bedford, Mass.) with excitation at 485 nm and emission at 530 nm.

Western Blots:

Antibody sources were as follows: Antibodies specific for ETC Complex IV, subunits I, II and IV. were from Molecular Probes, Inc. (Eugene, Oreg.): antibodies specific for ATP synthase subunit 8 were generously provided by Dr. Russell Doolittle (Univ. California San Diego). Equal amounts of SMP protein or "total lysate" from skeletal muscle biopsy preparations or from cultured cells, prepared as described above, were subjected to SDS polyacrylamide gel electrophoresis on 4–10% gels (Niovex, San Diego, Calif.). The proteins were electroblot transferred to Hybond ECL nitrocellulose (Amersham, Buckinghamshire, England) using standard procedures, and probed with each of the above antibodies. Bands were visualized using an ECL Western Blot Analysis System (Amersham, Buckinghamshire, England) according to the supplier's instructions. Band densities were measured by scanning the autoradiograms, and quantitative data obtained from the scans using National Institutes of Health Image Analysis software (NIH, Bethesda, Md.).

RESULTS:

Cybrid Cell Studies:

Cybrid cell lines were constructed as described above, using platelets from either healthy control volunteer subjects or from age-matched volunteers diagnosed as having NIDDM according to criteria provided herein (e.g. Gavin et al. 1999 (*Diabetes Care* 22(suppl. 1):S5–S19). Mitochondrial function of the cybrids was assessed in several ways:

Production of Reactive Oxygen Species.

The production of reactive oxygen species was measured in cybrid and parental SH-SY5Y cells. All results were expressed relative to the parental cells. There was a dramatic increase in reactive oxygen species in NIDDM cybrids as compared to cybrids constructed using mitochondria from control subjects (FIG. 1). This finding suggested that mitochondrial function was abnormal in the NIDDM cybrids, and that the abnormality had been transferred to the cultured cells through the donor mitochondria.

Mitochondrial Enzyme Activities.

Mitochondrial electron transport enzyme activities were measured in control and NIDDM cybrid cells. As shown in Table 1, complex I and IV activities were equal in control and NIDDM cybrids. In contrast, ATP synthase (complex V) activity was decreased 35% in the NIDDM cybrids.

TABLE 1

MITOCHONDRIAL ENZYME ACTIVITIES IN CONTROL AND NIDDM CYBRID CELLS

| Cybrid | ETC Complex I (μM/min/mg) | ETC Complex IV (min$^{-1}$ mg$^{-1}$) | ATP Synthase (nmol/min/mg) |
|---|---|---|---|
| Control | 27.5 ± 1.2 | 2.05 ± 0.06 | 17.2 ± 1.2 |
| NIDDM | 26.6 ± 0.8 | 1.92 ± 0.29 | 11.2 ± 0.88* |

*$p < 0.05$ vs. control

Human Skeletal Muscle Studies:

To confirm the abnormalities observed in cybrid cells, selected mitochondrial enzyme activities and content were measured in human skeletal muscle from a similar patient population that included individuals with NIDDM, lean controls, and age- and weight-matched controls.

Enzyme Activities.

Figure 2:
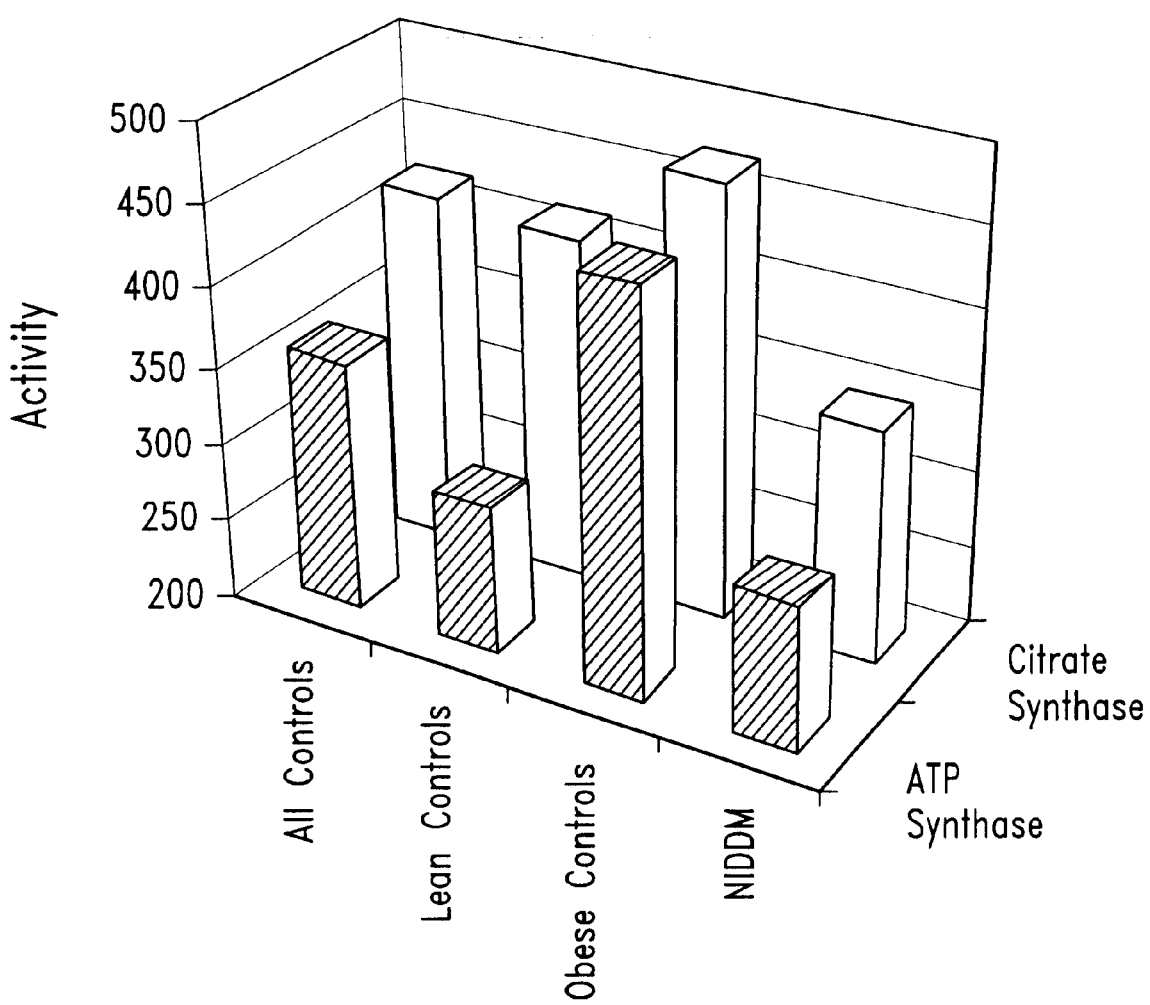
FIG. 2 depicts levels of enzyme catalytic activity in skeletal muscle biospsies for two mitochondrial enzymes involved in ATP synthesis, ATP synthetase and citrate synthase.

ATP synthase activity of SMP perparations of NIDDM muscle was decreased 36% as compared to controls (FIG. 2, Tables 2–3). Citrate synthase activity measured in the crude lysates was decreased by 26% as compared to controls. While citrate synthase activity did not differ significantly between lean and obese (weight-matched to NIDDM population), ATP synthase activity was higher in obese (weight-matched to NIDDM) than in lean individuals (FIG. 2, Tables 2–3).

TABLE 2

MITOCHONDRIAL ENZYME ACTIVITIES IN CONTROL AND NIDDM SKELETAL MUSCLE-PER UNIT MITOCHONDRIAL PROTEIN

| Cybrid | ETC Complex V (nmol/min/mg) | ETC Complex IV (min$^{-1}$ mg$^{-1}$) | Citrate Synthase (M/min/mg) |
|---|---|---|---|
| Control | 452 ± 72 | 13.5 ± 4.5 | 4.6 ± 0.6 |
| NIDDM | 288 ± 29 | 5.4 ± 1.7 | 3.5 ± 0.3 |

TABLE 3

MITOCHONDRIAL ENZYME ACTIVITIES IN CONTROL AND NIDDM SKELETAL MUSCLE-PER UNIT TOTAL MUSCLE LYSATE PROTEIN

| Cybrid | ETC Complex V (nmol/min/mg) | ETC Complex IV ($min^{-1}$ $mg^{-1}$) | Citrate Synthase (M/min/mg) |
|---|---|---|---|
| Control | 5.4 ± 1 | 1.6 ± 0.2 | 154 ± 20 |
| NIDDM | 5.0 ± 0.7 | 0.74 ± 0.3 | 127 ± 7.5 |

Enzyme Content of Skeletal Muscle.

Figure 3A:
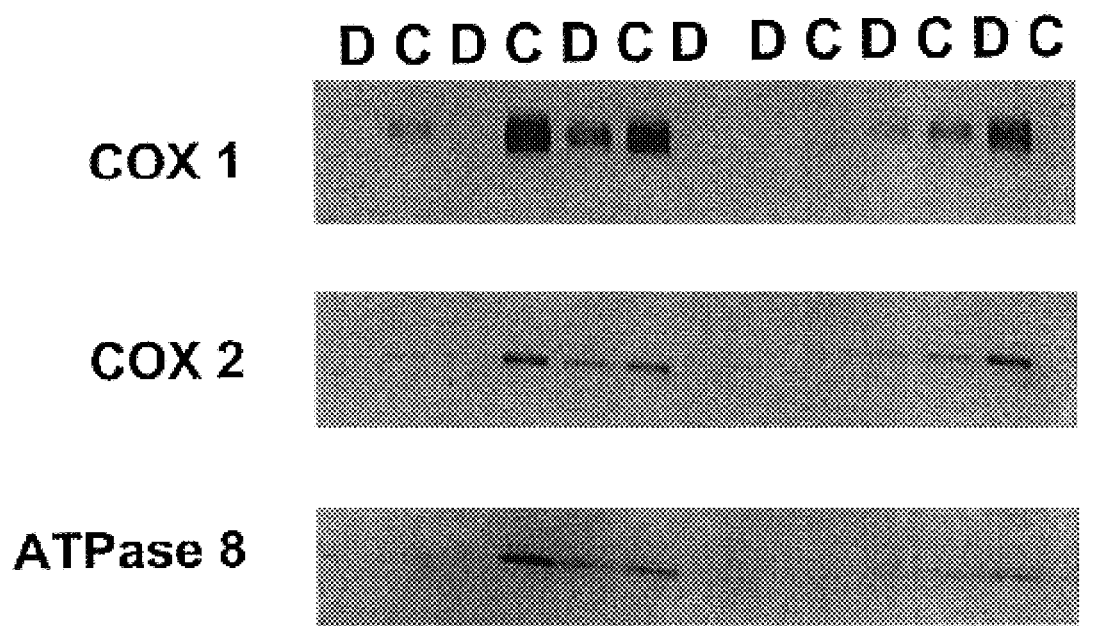
FIG. 3 shows relative quantities in skeletal muscle biopsies of the mitochondrial enzymes involved in ATP synthesis ATP synthetase subunit 8, cytochrome c oxidase subunit 1 and cytochrome c oxidase subunit 2.
Figure 3B:
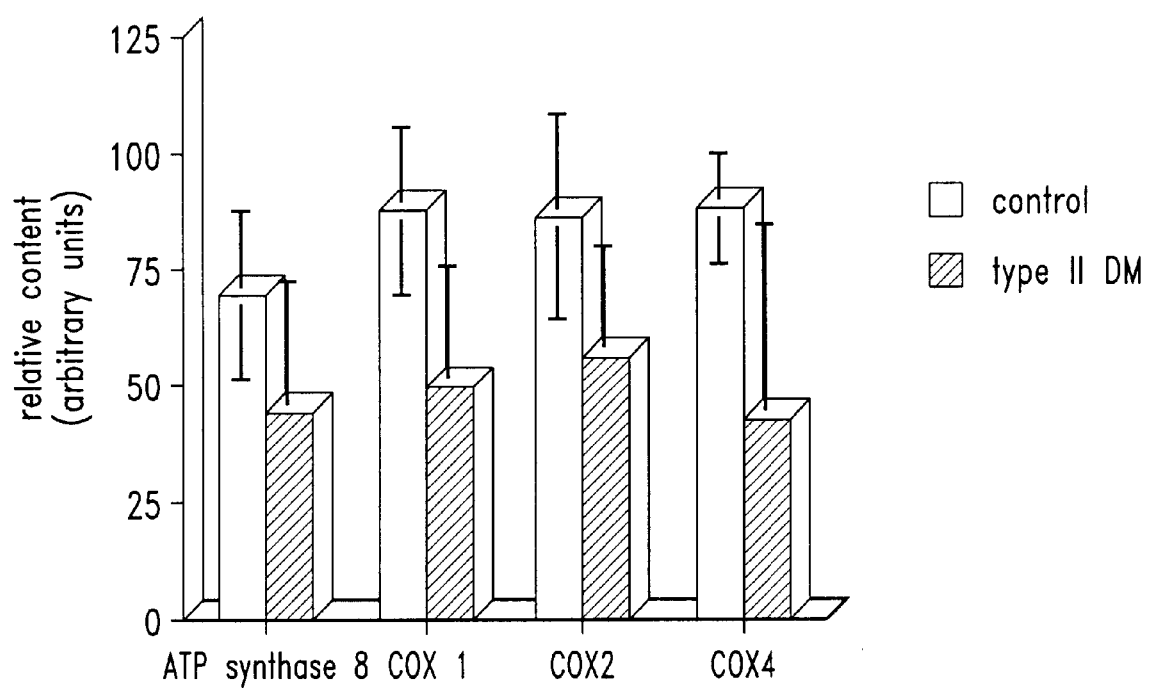

To determine whether the decreased ATP synthase activity in NIDDM was due to lower content of the enzyme, western blot analyses were performed using SMP preparations of skeletal muscle biopsies as described above. Mitochondrial-encoded ATP synthase subunit 8 was measured. In addition, the contents of several other respiratory enzyme subunits were determined: cytochrome c oxidase subunits 1 and 2 (mitochondrial DNA-encoded), and cytochrome c oxidase subunit 4 (nuclear-encoded). As shown in FIG. 3, the content of ATP synthase subunit 8 was lower on average in NIDDM than in control SMP preparations. Similarly, all cytochrome oxidase subunits were decreased on average in NIDDM as compared to controls (subunit 1 decreased 51%; subunit 2 decreased 37%; subunit 4 decreased 37%).

Example 2

DETERMINATION OF CELLULAR ATP CONTENT AS AN INDICATOR OF ALTERED MITOCHONDRIAL FUNCTION

Type 2 diabetes mellitus is characterized by both impaired insulin secretion and insulin resistance in peripheral tissues such as skeletal muscle and adipose tissue. That is, glucose is taken up by cells and metabolized inefficiently in response to insulin in type II diabetes. This example shows that normal insulin-mediated glucose metabolism is dependent upon normal mitochondrial function and in particular, mitochondrial ATP production, An model of an altered mitochondrial function, specifically, defective mitochondrial ATP production, is introduced into cultured skeletal muscle cells and adipocytes by contacting these cells with an inhibitor of electron transport.

Cell Culture:

L6 rat skeletal muscle cells and 3T3-L1 mouse cells were purchased from American Type Culture Collection (ATCC; Rockville, Md.). L6 cells were maintained in Dulbecco's Modified Eagle's Medium (DMEM, Irvine Scientific, Irvine, Calif.) that contained 10% fetal calf serum (Irvine Scientific), 2 mM glutamine, 100 IU/ml penicillin, and 100 µg/ml streptomycin. The L6 cells were differentiated to myotubules by growing in the same media with fetal calf serum reduced to 2% for 3–4 days. The 3T3-L1 cells were maintained in DMEM with 10% fetal calf serum (Hyclone, Logan, Utah). 2 mM glutamine, 100 IU/mi penicillin, and 100 µg/ml streptomycin. Upon reaching confluence, the fibroblast-like cells were differentiated to the adipocyte form by addition of 0.1 mg/ml isobutylmethylxanthine, 25 RM dexamethasone, and 5 µg/ml insulin for 2 days. The cells were than grown in the maintenance media plus 1 µg/ml insulin until fully differentiated.

Deoxyglucose Uptake:

Cells were grown to confluence in 35 mm dishes and differentiated as described above. The cells were rinsed with HBSS, then incubated for 1 hr at 37° C., in Krebs-Ringer-HEPES buffer (KRH: 131 MM NaCl, 4.7 MM KCl, 2.5 MM $CaCl_2$, 1.24 mM $MgSO_4$, 2.5 mM $NaH_2PO_4$, 10 mM HEPES, 0.5% BSA; pH 7.4). Fresh KRH (1 ml) was then added along with insulin (various concentrations) and experimental agents of choice. The cells were incubated an additional 30 min at 37° C., after which [$^3$H]2-deoxyglucose (2-DOG: New England Nuclear, Boston, Mass.) was added to a final concentration of 0.1 mM. After 5 min, the medium was rapidly aspirated, and the cells washed three times with HBSS. The cells were then solubilized in 1 N NaOH, neutralized with HCl, and transferred to scintillation vials for counting in a Beckman scintillation counter.

Whole-Cell Insulin Receptor and Receptor Substrate Phosphorylation Assays:

The phosphorylation in response to insulin of the insulin receptor and its substrate. IRS-1, was measured in whole cells using a western blotting technique. Cells were grown to confluence and differentiated in 35 mm tissue culture dishes. The cells were starved overnight by culturing in their usual maintenance media lacking serum. The cells were then rinsed with KRH, and KRH buffer containing insulin (various concentrations) and/or experimental compounds (e.g., KCN) was added to the cells for 2 min at 37° C. The buffer was quickly aspirated, the cells rinsed with ice-cold KRH, and SDS-PAGE sample buffer (Novex: San Diego, Calif.) added directly to the dishes. The lysed cells were collected by pipettina, boiled, and subjected to SDS-PAGE on 4–20% gels (Novex; San Diego, Calif.). Separated proteins were then electrophoretically transferred to nitrocellulose membranes (HyBond: Amersham: Buckinghamshire, England). The blots were incubated with anti-phosphotyrosine antibody (Upstate Biotechnology; Lake Placid, N.Y.) and visualized using the chemiluminescent ECL western Blotting Kit (Amersham, Cleveland, Ohio), both according to the suppliers' recommendations.

ATP Content of Intact Cells:

ATP was measured in cultured cells by first extracting the pyridine nucleotides, then performing a luciferase-based assay to quantify ATP. Briefly, ice-cold 5% trichloroacetic acid (TCA) was added to cultured cells, and the extracts collected by scraping from the dishes. Ten volumes of diethyl ether were added to each sample to remove residual ether; the aqueous phase containing ATP was collected. The extraction was repeated 3 times. One volume buffer A (40 mM HEPES, 3 mM $MgCl_2$; pH 8.0) was added. ATP in the extracts was measured as follows. An aliquot of each sample was transferred to a 96-well plate and diluted as needed with PBS to yield a final volume of 100 µl per well. Luciferase solution (Boehringer-Mannheim, Indianapolis, Ind.; 30 µl; 2 µg/ml in 50 mM Tris, pH 7.75; 2 mM EDTA; 60 mM dithiothreitol; 10 mM 5 $MgSO_4$; 0.075% BSA) was added, followed by 30 µl 41 luciferin solution (Boebringer-Mannheim, Indianapolis, Ind.; 35 µM in the above buffer). The reaction was allowed to proceed for 15 min at room temperature. Luminescence was then read on a CytoFluor plate reader (Millipore; Bedford, Mass.).

Results:

L6 cells were differentiated to myotubes and glucose transport assays were conducted in the absence or presence of KCN. Initial KCN dose-response studies established KCN concentrations that did not affect basal (non-insulin stimulated) glucose transport but that did inhibit insulin-stimulated glucose transport. In subsequent assays, KCN was used at the selected concentration (0.5 mM). In the presence of KCN, cellular ATP levels decreased by 39.3%±8.3 under basal conditions, relative to ATP levels in the absence of KCN. Also, in the presence of KCN, cellular ATP levels decreased by 25.7%±1.2 under insulin-stimulated conditions, relative to controls. Glucose transport studies showed that KCN had no significant effect on basal alucose transport (14% increase in transport relative to controls), but that under insulin-stimulated conditions, KCN inhibited glucose transport significantly, as evidenced by a 61% decrease relative to controls. Mitochondrially produced ATP may therefore be required for insulin-stimulated glucose transport but not for basal glucose transport.

What is claimed is:

1. A method for identifying a risk for Type 2 diabetes in a human subject, comprising:

comparing the level of at least one indicator of altered mitochondrial function in a biological sample from the subject with a control sample; and therefrom identifying the risk for Type 2 diabetes.

2. A method for determining a degree of disease progression in a human subject having Type 2 diabetes, comprising:

comparing the level of at least one indicator of altered mitochondrial function in each of first and second biological samples said first and second biological samples being obtained from said subject at a first time point and a second time point, respectively; and therefrom determining the degree of progression of Type 2 diabetes.

3. The method of any one of claims 1 or 2 wherein the indicator of altered mitochondrial function is a mitochondrial electron transport chain enzyme.

4. The method of claim 3 wherein the step of comparing comprises measuring electron transport chain enzyme catalytic activity.

5. The method of claim 4 wherein the step of measuring comprises determining enzyme activity per mitochondrion in the sample.

6. The method of claim 4 wherein the step of measuring comprises determining enzyme activity per unit of protein in the sample.

7. The method of claim 3 wherein the step of comparing comprises measuring electron transport chain enzyme quantity.

8. The method of claim 7 wherein the step of measuring comprises determining enzyme quantity per mitochondrion in the sample.

9. The method of claim 7 wherein the step of measuring comprises determining enzyme quantity per unit of protein in the sample.

10. The method of any one of claims 1 or 2 wherein the indicator of altered mitochondrial function is a Krebs cycle enzyme.

11. The method of claim 10 wherein the step of comparing comprises measuring Krebs cycle enzyme catalytic activitye.

12. The method of claim 11 wherein the step of measuring comprises determining enzyme activity per mitochondrion in the sample.

13. The method of claim 11 wherein the step of measuring comprises determining enzyme activity per unit of protein in the sample.

14. The method of claim 10 wherein the step of comparing comprises measuring Krebs cycle enzyme quantity.

15. The method of claim 14 wherein the step of measuring comprises determining enzyme quantity per mitochondrion in the sample.

16. The method of claim 14 wherein the step of measuring comprises determining enzyme quantity per unit of protein in the sample.

* * * * *

UNITED STATES PATENT AND TRADEMARK OFFICE
CERTIFICATE OF CORRECTION

PATENT NO. : 6,280,966 B1  
DATED : August 28, 2001  
INVENTOR(S) : Christen M. Anderson and Robert E. Davis Page 1 of 1

It is certified that error appears in the above-identified patent and that said Letters Patent is hereby corrected as shown below:

<u>Column 36, claim 11,</u>  
Lines 17 and 18, "enzyme catalytic activitye" should read -- enzyme catalytic activity --.

Signed and Sealed this

Twenty-sixth Day of February, 2002

*Attest:*

JAMES E. ROGAN  
*Attesting Officer*   *Director of the United States Patent and Trademark Office*